US010458965B1

(12) United States Patent
Iyer et al.

(10) Patent No.: US 10,458,965 B1
(45) Date of Patent: Oct. 29, 2019

(54) DEVICE AND SYSTEM FOR OPTICALLY ANALYZING FOOD PRODUCTS

(71) Applicant: P & P OPTICA INC., Waterloo (CA)

(72) Inventors: Krishna Iyer, Waterloo (CA); Olga Ewa Pawluczyk, Waterloo (CA); Bradley Oldenburg, Waterloo (CA); Simon Guthrie, Waterloo (CA); Timothy M. F. Stork, Kitchener (CA); Ewa Osika, Cambridge (CA); David William Lizius, Guelph (CA); Romuald Pawluczyk, Conestogo (CA); Anthony Robert Shaw, Waterloo (CA); Alexander Baran-Harper, Waterloo (CA)

(73) Assignee: P & P OPTICA INC., Waterloo, Ontario (CA)

( * ) Notice: Subject to any disclaimer, the term of this patent is extended or adjusted under 35 U.S.C. 154(b) by 0 days.

(21) Appl. No.: 15/998,434

(22) Filed: Aug. 15, 2018

(51) Int. Cl.
*G01N 33/02* (2006.01)
*G01N 21/3563* (2014.01)
*G01N 21/25* (2006.01)
*G01N 21/88* (2006.01)
G01N 21/84 (2006.01)
G01N 21/17 (2006.01)

(52) U.S. Cl.
CPC .......... *G01N 33/02* (2013.01); *G01N 21/251* (2013.01); *G01N 21/3563* (2013.01); *G01N 21/88* (2013.01); G01N 2021/1765 (2013.01); G01N 2021/845 (2013.01)

(58) Field of Classification Search
CPC combination set(s) only.
See application file for complete search history.

(56) References Cited

U.S. PATENT DOCUMENTS

| 6,587,575 B1 * | 7/2003 | Windham | G01N 21/31 |
| | | | 250/458.1 |
| 2007/0038040 A1 * | 2/2007 | Cense | A61B 3/1005 |
| | | | 600/310 |

(Continued)

OTHER PUBLICATIONS

IDS, "Line scan mode represents a cost-effective alternative to a line scan camera" https://en.ids-imaging.com/technical-article/en_tech-article-linescan-mode.html, Jul. 13, 2017 (Year: 2017).*

(Continued)

*Primary Examiner* — Maurice C Smith
(74) *Attorney, Agent, or Firm* — Perry + Currier Inc.

(57) ABSTRACT

A device and system for optically analyzing food products is provided. The device comprises first and second imaging devices respectively sensitive to first and second wavelengths; the imaging devices include a line-scan camera to acquire images of food products at a line in a food-path-facing direction, and a line-scan spectrometer to acquire spectroscopic images at the line. The device includes an optical filter configured to: convey the first wavelengths from the line to the first imaging device; and convey the second wavelengths from the line to the second imaging device. The device includes a frame to align the optical filter and respective optical axes of the first and second imaging devices, relative to each other and the food-path-facing direction, such that the first imaging device and the second imaging device are optically aligned via the optical filter to image the line.

16 Claims, 19 Drawing Sheets

(56) References Cited

U.S. PATENT DOCUMENTS

| | | | |
|---|---|---|---|
| 2008/0239307 A1* | 10/2008 | Talley | G01J 3/02 356/301 |
| 2009/0080706 A1* | 3/2009 | Tao | G01N 21/94 382/110 |
| 2012/0050733 A1* | 3/2012 | Takimoto | G01J 3/44 356/301 |
| 2013/0293882 A1* | 11/2013 | Dottery | G01J 3/44 356/301 |
| 2016/0207071 A1* | 7/2016 | Cohn | B07C 5/3425 |
| 2018/0180642 A1* | 6/2018 | Shetty | G01Q 30/025 |
| 2018/0344228 A1* | 12/2018 | Yelin | A61B 5/441 |

OTHER PUBLICATIONS

Jianwei Qin, "Line-Scan Hyperspectral Imaging Techniques for Food Safety and Quality Applications", Jan. 26, 2017, Applied Science (Year: 2017).*

* cited by examiner

DEVICE AND SYSTEM FOR OPTICALLY ANALYZING FOOD PRODUCTS

BACKGROUND

Imaging of food products to determine quality, and the like, can be challenging. In some approaches cameras acquire images of food products being conveyed (e.g. in a factory) using a conveyor. However, simple camera images of the food products may not yield enough information to accurately determine quality. While imaging devices other than cameras may be mounted down the line from a camera on a conveyor, data acquired from such imaging devices needs to be coordinated with the camera images. However, as many food products look similar, it can be challenging to coordinate such data with the camera images.

BRIEF DESCRIPTIONS OF THE DRAWINGS

For a better understanding of the various embodiments described herein and to show more clearly how they may be carried into effect, reference will now be made, by way of example only, to the accompanying drawings in which.

DETAILED DESCRIPTION

An aspect of the specification provides a device for optically analyzing food products, the device comprising: a first imaging device sensitive to first wavelengths; a second imaging device sensitive to second wavelengths, one of the first imaging device and the second imaging device comprising: a line-scan camera configured to acquire images of food products in a human-visible wavelength spectrum, at a line in a food-path-facing direction, and an other of the first imaging device and the second imaging device comprising: a line-scan spectrometer configured to acquire spectroscopic images of the food products from the line in the food-path-facing direction; an optical filter configured to: convey the first wavelengths from the line to the first imaging device; and convey the second wavelengths from the line to the second imaging device; and a frame configured to align the optical filter and respective optical axes of the first imaging device and the second imaging device, relative to each other and the food-path-facing direction, such that the first imaging device and the second imaging device are optically aligned via the optical filter to image the line.

Figure 1A:
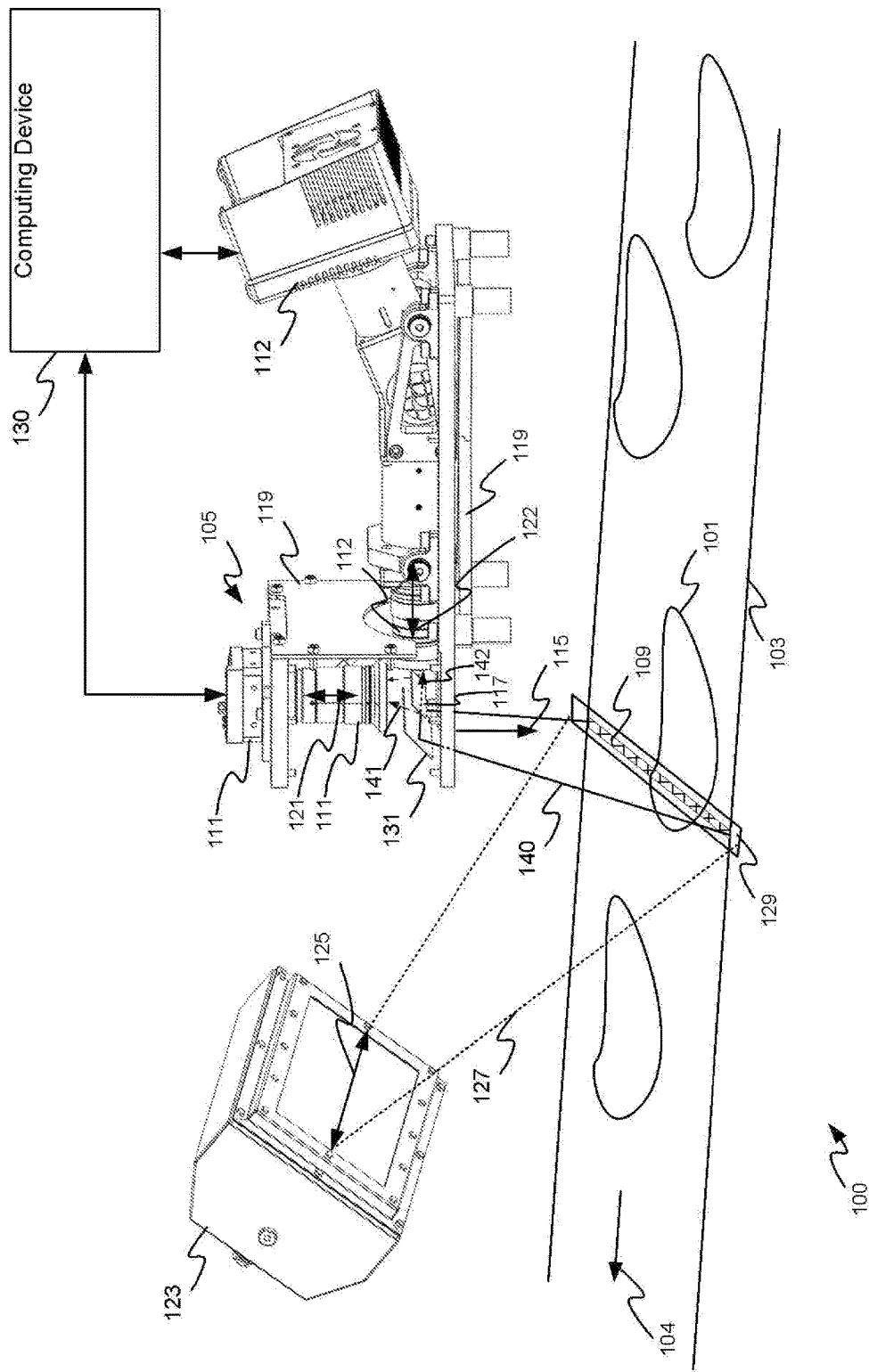
FIG. 1A depicts is a schematic perspective view of a device and system for optically analyzing food products, according to non-limiting examples.
Figure 1B:
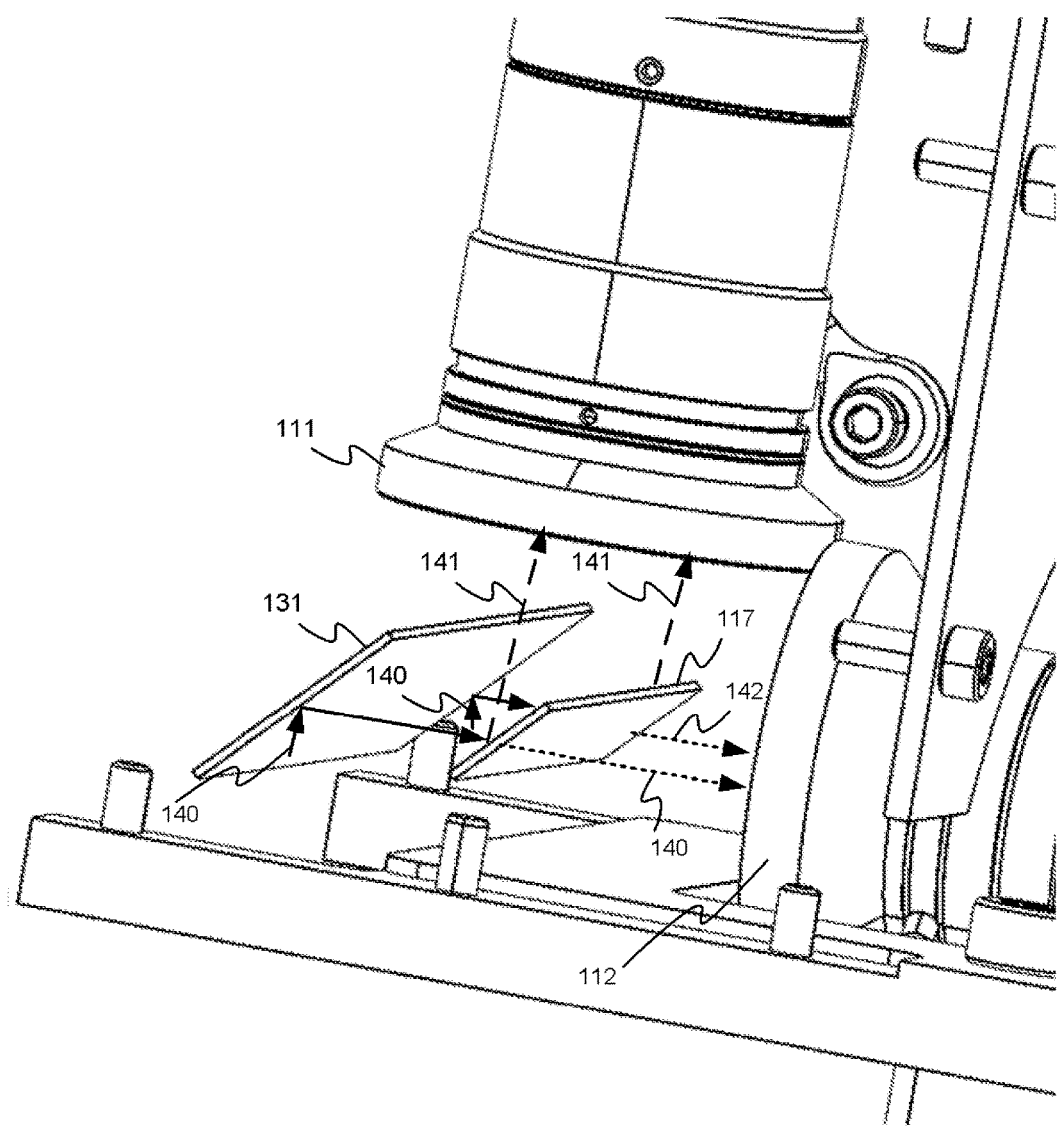
FIG. 1B depicts detail of a fold mirror and optical filter of the system of FIG. 1B, according to non-limiting examples.

Attention is directed to FIG. 1A, which depicts respectively a system 100 for optically analyzing food products 101, for example in a food product manufacturing environment and/or food product processing environment and/or food packaging environment, and the like, and FIG. 1B which depicts details of a fold mirror and optical filter of the system 100 in relation to imaging devices. As depicted the food products 101 are being conveyed along a food product path such as a conveyor 103 and the like, for example in a food product path direction 104 (e.g. from right to left with respect to FIG. 1), the food products 101 being optically analyzed while being conveyed on the conveyor 103. While the food products 101 are depicted as slabs (e.g. meat), the food products 101 may include any type of food product such as meat, fruit, vegetables, and the like. While the conveyor 103 is configured to convey the food products 101 in a horizontal direction, in other examples, the conveyor 103 may convey the food products 101 in a non-horizontal direction, for example at an angle upwards or downwards. Indeed, when the food products are conveyed at an angle downwards, the conveyor 103 and/or a food product path may comprise a chute, and the like, along which the food products slide. Alternatively, as described in more detail below, the system 100 may include the food products 101 being conveyed in a waterfall food product path such that the food products 101 fall, for example from a first conveyor to a second conveyor, the food products 101 being optically analyzed while falling (e.g. the food product path direction 104 may alternatively be in a downward direction). Alternatively, the conveyor 103 may include a gap (e.g. the conveyor 103 may include two conveyors with a gap therebetween) and the food products 101 may be optically analyzed from below, through the gap. While present examples are described with respect to a conveyor, a conveyor may interchangeably be referred to herein as a food product path Regardless, in present examples, the food products 101 are generally conveyed along a food product path and optically analyzed at the food product path.

Hence, the system 100 further comprises a device 105 for optically analyzing the food products 101, for example at a line 109 located at the conveyor 103. The device 105 comprises: a first imaging device 111 sensitive to first wavelengths; a second imaging device 112 sensitive to second wavelengths, each of the first imaging device 111 and the second imaging device 112 configured to image the food products 101 from the line 109 in a food-path-facing direction 115 (e.g. a direction facing a food product path, such as a direction of the conveyor 103 relative to the device 105); an optical filter 117 configured to: convey the first wavelengths from the line 109 to the first imaging device 111, and convey the second wavelengths from the line 109 to the second imaging device 112; and a frame 119 configured to align the optical filter 117 and respective optical axes 121, 122 of the first imaging device 111 and the second imaging device 112, relative to each other and the food-path-facing direction 115, such that the first imaging device 111 and the second imaging device 112 are optically aligned via the optical filter 117 to image the line 109. As depicted, the food-path-facing direction is parallel to, and/or aligned with, the optical axis 121 of the first imaging device 111.

While not depicted, the device 105 may further include an enclosure compatible with a food packaging environment, and in which the other components of the device 105 are enclosed. Such an enclosure will be described in further detail below with respect to FIG. 8.

As depicted, the line 109 being imaged by each of the first imaging device 111 and the second imaging device 112 is located at the conveyor 103, in the food-path-facing direction 115 relative to both the respective optical axes 121, 122 of the first imaging device 111 and the second imaging device 112, and the optical filter 117, the line 109 located at the conveyor 103 about perpendicular to the food product path direction 104. Hence, the first imaging device 111 and the second imaging device 112 each generally simultaneously image the food products 101 at the line 109 as they are conveyed along the conveyor 103.

However, the line 109 need not be strictly perpendicular to the food product path direction 104 and may be at any suitable angle thereto. However, the line 109 generally extends from side-to-side across the conveyor 103, though the orientation and/or dimensions of the line 109 is generally defined by the optics of the imaging devices 111, 112, which generally focus the imaging devices 111, 112 at the line 109.

As depicted, the system 100 further comprises a lamp 123 for illuminating food products at a line, and the lamp 123 generally has a light emitting side with a length longer than a width, and/or is rectangular. Hence, the lamp 123 a light emitting side of the lamp 123 has a longitudinal axis 125, and the lamp 123 is generally configured to emit light 127 along the longitudinal axis 125, for example in a line and/or over a rectangular area along the longitudinal axis 125. Furthermore, the lamp 123 is generally positioned and/or angled to illuminate, and/or uniformly illuminate, an area 129 at the conveyor 103 that includes the line 109. Hence, the light 127 illuminates the food products 101 at the line 109 as they pass through the area 129, when being conveyed by the conveyor 103. The lamp 123 will be described in more detail below, however, the lamp 123 is generally configured to illuminate the area 129 uniformly, and hence may generally comprise an elongated reflector (including, but not limited to, an elliptical reflector, and the like) positioned in the lamp 123 along the longitudinal axis 125 and relative to a light source of the lamp 123, such that the reflector focuses the light 127 from the line 109. The lamp 123 is further generally compatible with a food product manufacturing environment and/or food product processing environment and/or food packaging environment, and the like, and includes a transparent polymer film which provides the food products 101 with protection from any glass that may shatter within the lamp 123.

While not depicted, the device 105 and the lamp 123 may be mounted relative to each other and the conveyor 103 using a support structure in a housing through which the conveyor 103 conveys the food products 101, and the like; such a housing is generally compatible with a food product manufacturing environment and/or food product processing environment and/or food packaging environment, and the like, and the like The light 127 emitted by the lamp 123 generally includes light in the first wavelength range at which the first imaging device 111 is sensitive, and includes light in the second wavelength range at which the second imaging device 112 is sensitive.

For example, as depicted, the first imaging device 111 comprises: a line-scan camera configured to acquire images of the food products 101 in a human-visible wavelength spectrum (e.g. which may include wavelengths within a range of about 390 nm to about 700 nm), from the line 109 in the food-path-facing direction 115. Hence, as depicted, the first imaging device 111 may comprise a charge-coupled device (CCD) line-scan camera, a video line scan camera, and the like, with suitable lenses, and the like, for acquiring line images of the food products 101 as they move along the conveyor 103, for example in the food product path direction 104. Specifically, the images of the food products 101 acquired by the line-scan camera generally comprise line-scan images of the food products 101 which may be merged and/or stitched together, and the like to form images of the food products 101; and/or the line-scan images may be analyzed without merging.

For example, as depicted, each of the first imaging device 111 and the second imaging device 112 are each in communication with a computing device 130 via respective wired and/or wireless links (depicted as arrows therebetween). In these examples, the computing device 130 receives the line-scan images from the line scan camera for analysis. The computing device 130 may merge and/or stitch together the line images to form images of the food products 101; and/or computing device 139 may analyze the line-scan images without merging.

As depicted, the second imaging device 112 comprises: a line-scan spectrometer configured to acquire spectroscopic images of the food products 101 at the line 109 in the food-path-facing direction 115. The line-scan spectrometer is generally configured to determine wavelengths of light present in the food products 101, when the food products 101 are at the line 109. Furthermore, acquisition of images and/or spectroscopic images by the first imaging device 111 and the second imaging device 112 may occur according to a given resolution along the length of the line 109 and/or according to a given resolution in a direction of the food product path direction 104 and/or and wavelength range of the second imaging device 112.

The given resolution along the length of the line 109 may be less than 1 mm along the length of the line 109, however the given resolution may depend on one or more of: a length of the line 109, which may depend on a width of the conveyor 103 (and the like) and/or a width of a region being images (e.g. the line 109 may be less than the width of the conveyor 103); a resolution of the first imaging device 111 and/or the second imaging device 112; and the like. The given resolution in a direction of the food product path direction 104 may depend on one more of a frame rate of the first imaging device 111 and/or the second imaging device 112; a speed of the conveyor 103 (e.g. how fast the food products 101 move through the line 109 and/or what portion of the first imaging device 111 and/or the second imaging device 112; and the like. Furthermore post processing of images acquired by the first imaging device 111 and/or the second imaging device 112 may affect resolution, including, but not limited to, pixel binning.

For example, the line-scan spectrometer may determine a spectrum of wavelengths present in each of a plurality of segments of the line 109 (e.g. each of the plurality of segments may be less than 1 mm and/or in accordance with the given resolution along the line 109) by: acquiring light from segments of the line 109 (e.g. via the optical filter 117 and using lenses, and the like (as described below); dispersing the light in each of the segments using a transmission grating and/or a holographic transmission grating, and the like; and measuring wavelengths of the dispersed light of each of the segments using, for example, a plurality of light detectors disposed in an array and positioned to receive the dispersed light of each of the segments from the transmission grating and/or the holographic transmission grating, and the like. The resulting wavelength spectra may be referred to interchangeably as spectroscopic images and/or spectroscopic line-scan images. The sensitivity of the line-scan spectrometer may be in any suitable wavelength range defined by the transmission grating and/or a holographic transmission grating, and the like, including, but not limited to, infrared wavelengths and/or wavelengths in range of about 800 nm to 2000 nm. Furthermore, the array of light detectors may be arranged to detect discrete wavelengths and/or a continuum of wavelengths (e.g. at least according to a given resolution).

Such spectroscopic images of the food products 101 may be transmitted to the computing device 130 for analysis to determine quality of the food products 101 in the segments of the line 109. For example, various successful prototypes have shown that food impurities and/or contaminants such as plastic, fingernail clippings and the like have signature spectra in a range of about 800 nm to 2000 nm; similarly, meat products, protein, fat, bone, cartilage, etc., have signature spectra in a range of about 800 nm to 2000 nm; similarly, fruits and vegetables, and/or other types of food products, have signature spectra in a range of about 800 nm to 2000 nm. Hence, by comparing a spectroscopic image of a segment of the line 109 with predetermined signature spectra of different types of impurities and/or contaminants and/or different types of food product types, a quality of the food product 101 can be determined on a segment-by-segment basis from the line 109.

Furthermore, as the computing device 130 receives both the images from the line-scan camera and the spectroscopic images from the line-scan spectrometer, and as the images from the line-scan camera and the spectroscopic images from the line-scan spectrometer are acquired simultaneously from the line 109, as described hereafter, the quality of food products 101 may be determined in the segments of the line 109 and coordinated with the images of the line 109, for example to generate images that show quality regions of the food products 101. For example, when the food products 101 comprise meat slabs, images of the meat slabs may be generated that show locations of protein, protein, fat, bone, cartilage and impurities and/or contaminants such as plastic, finger nail clippings and the like. The meat slabs may then be sorted by quality and/or meat slabs with impurities may be visually identified and removed from the conveyor 103, using an automatic meat sorting system and/or by hand (e.g. assuming a notification device provides a notification of contamination and/or quality of a meat slab). Similar sorting may occur for other types of food products. An example of such a determination is described below with respect to FIG. 9.

Paths of light in the system 100 will now be described. As depicted, the frame 119 is configured to support and/or hold the first imaging device 111 and the second imaging device 112 such that the respective optical axes 121, 122 of the first imaging device 111 and the second imaging device 112 are at about 90° to each other, and the optical filter 117 is at about 45° to each of the respective optical axes 121, 122 of the first imaging device 111 and the second imaging device 112.

As depicted, the device 105 further comprises a fold mirror 131 parallel to the optical filter 117. In these examples, the location of the fold mirror 131 generally defines the location of the line 109. Hence, the frame 119 supports and/or holds the components of the device 105, including the fold mirror 131, in alignment and the device 105 is generally held relative to the conveyor 103 to define a suitable location of the line 109, for example using a support structure of a housing. While components of the frame 119 that support and/or hold the fold mirror 131 and the optical filter 117 in alignment with each other and the other components of the device 205 are not depicted (e.g. so that the fold mirror 131 and the optical filter 117 are viewable in FIG. 1), they are nonetheless understood to be present.

The device 105 is mounted over the conveyor 103 such that the fold mirror 131 defines the position of the line 109 at the conveyor 103, with the line 109 being below the fold mirror 131. The fold mirror 131 is generally mounted at a 45° angle to the conveyor 103 in the food-path-facing direction, and a longitudinal axis of the fold mirror 131 is about perpendicular to the food product path direction 104 and the respective optical axes 121, 122 of each of the imaging devices 111, 112. Furthermore, the device 105 is mounted over the conveyor 103 such that the imaging devices 111, 112 are focused at the line 109, for example via respective optical paths from the imaging devices 111, 112 to the optical filter 117, from the optical filter 117 to the fold mirror 131, and from the fold mirror 131 and to the line 109.

Hence, light 140 from the line 109 (e.g. as illuminated by the lamp 123) is reflected by the fold mirror 131 towards the optical filter 117 along the optical axis 122 of the second imaging device 112. The optical filter 117 may comprise a dichroic mirror and the like which separates the light 140 reflected by the fold mirror 131 into two paths. In general, a longitudinal axis of the optical filter 117 is parallel with the longitudinal axis of the fold mirror 131. Furthermore, the lengths of both the optical filter 117 and the fold mirror 131 are generally suitable for imaging the line 109.

Hence, as depicted, and as best scene in FIG. 1B, the optical filter 117 reflects light 141 of the first wavelengths from the fold mirror 131 to the first imaging device 111, for example at a 90° angle from the fold mirror 131 to the optical axis 121 of the first imaging device 111. In FIG. 1B, for clarity, only a portion of the light 140 as it reflects from the fold mirror 131 is depicted.

Also as best scene in FIG. 1B, the optical filter 117 further transmits light 142 of the second wavelengths to the second imaging device 112, for example along the optical axis 122 of the second imaging device 112. When the second wavelengths are longer than the first wavelengths, the optical filter 117 may comprise a cold mirror and/or a dichroic mirror which conveys and/or reflects the first wavelengths from the line 109 to the first imaging device 111; and conveys and/or transmits the second wavelengths from the line 109 to the second imaging device 112.

As the term "cold mirror" specifically refers to a mirror and/or a dichroic mirror which reflects a first range of wavelengths and transmits a second range of wavelengths longer than the first range of wavelengths, when the optical filter 117 comprises a cold mirror, it is understood that the first wavelengths (e.g. at which the first imaging device 111 is sensitive (are shorter than the second wavelengths (e.g. at which the second imaging device 112 is sensitive). Such examples hence include the depicted example in which the first imaging device 111 comprises a line-scan camera sensitive to human-visible wavelengths and the second imaging device 112 comprises a line-scan spectrometer sensitive to infrared wavelengths.

However, in other examples, the positions of the line-scan camera and the line-scan spectrometer may be reversed, and the cold mirror of the optical filter 117 may be replaced with a hot mirror which reflects the infrared wavelengths and transmits human-visible wavelengths.

Furthermore, the fold mirror 131 may be optional and/or removeable, with the reflection/transmission properties of the optical filter 117 adapted accordingly for the positions and respective wavelengths of the line-scan camera and the line-scan spectrometer.

Various optical configurations of the device 105 are described hereafter.

Figure 2:
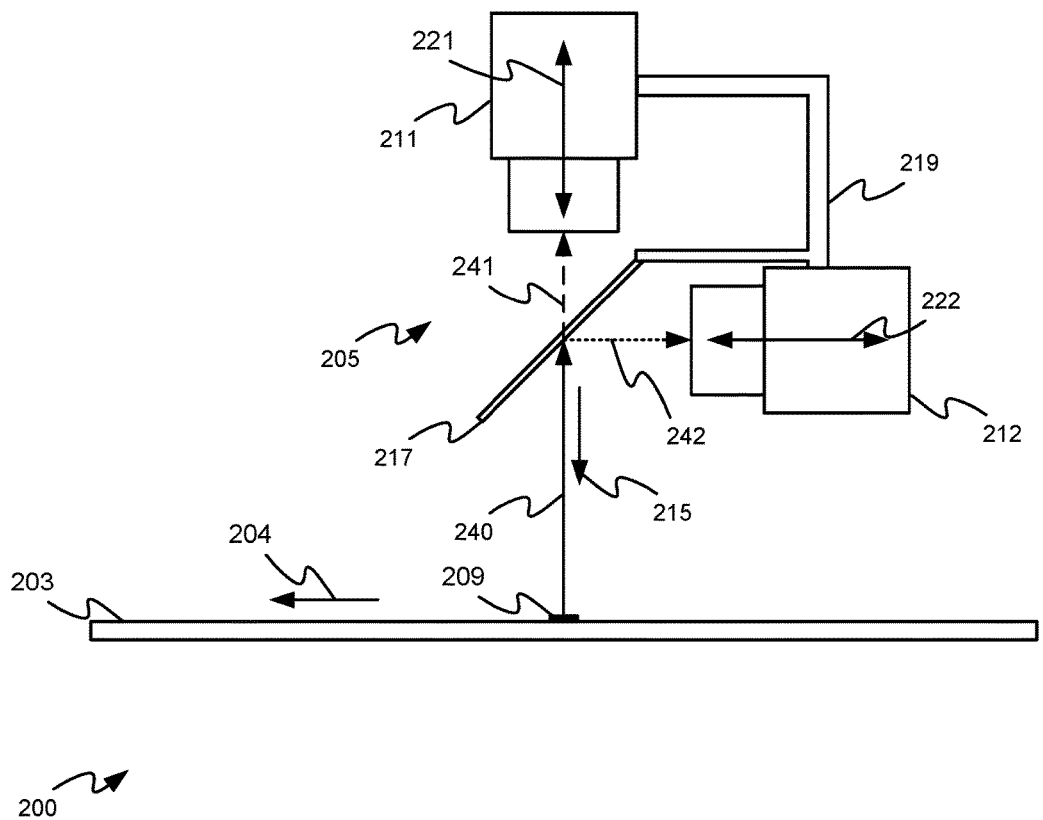
FIG. 2 depicts is a schematic view of a first optical configuration of a device for optically analyzing food products, according to non-limiting examples.

For example, attention is directed to FIG. 2 which depicts a schematic side view of a system 200 which is substantially similar to the system 100 with like components having like numbers, however in a "200" series rather than a "100" series.

The system 200 hence includes a food product path 203, where food products (not depicted) are conveyed in a food product path direction 204, and a device 205, similar to the device 105, for optically analyzing food products at a line 209 at the food product path 203. Indeed, the device 205 may represent one example of how the device 105 may be configured. While not depicted, the system 200 may include a lamp similar to the lamp 123 which illuminates the line 209, and a computing device similar to the computing device 130.

The device 205 is generally mounted relative to the food product path 203 along which food products are conveyed. The food product path 203 may comprise the conveyor 103 or another food product path, and the line 209 being imaged by the device 205, similar to the line 109, is located at the food product path 203, for example about perpendicular to the food product path 203 and/or the food product path direction 204. While only an end of the line 209 is depicted schematically (with some width simply to show position), the line 209 is understood to extend about perpendicularly across the food product path 203.

Furthermore, while in FIG. 2, the food product path 203 is depicted as "beneath" the device 205, the food product path 203 and the device 205 may be in any orientation relative to one another. For example, the food product path 203 and the device 205 may be rotated by an angle, relative to horizontal, for example when the food product path 203 comprises the conveyor 103 and/or a chute conveying food products in a non-horizontal direction. In other examples, the food product path 203 and the device 205 may be rotated by 90° such that the food product path 203 comprises a waterfall food product path in which food products fall from one conveyor to another, and the like. In yet further examples, the device 205 may be "beneath" the food product path 203, and the food product path 203 may comprise an aperture, and the like, through which food products conveyed along the food product path 203 may be imaged; in some of these examples, the food product path 203 may comprise two conveyors with a gap therebetween, the gap located at the line 209, and the device 205 positioned (e.g. beneath the food product path 203) to image food products through the gap.

Similar to the device 105, the device 205 comprises: a first imaging device 211 sensitive to first wavelengths; a second imaging device 212 sensitive to second wavelengths, one of the first imaging device 211 and the second imaging device 212 comprising: a line-scan camera configured to acquire images of food products in a human-visible wavelength spectrum, at a line 209 in a food-path-facing direction 215, and an other of the first imaging device 211 and the second imaging device 212 comprising: a line-scan spectrometer configured to acquire spectroscopic images of the food products from the line in the food-path-facing direction 215; an optical filter 217 configured to: convey the first wavelengths from the line 209 to the first imaging device 211; and convey the second wavelengths from the line 209 to the second imaging device 212; and a frame 219 (depicted schematically) configured to align the optical filter 217 and respective optical axes 221, 222 of the first imaging device 211 and the second imaging device 212, relative to each other and the food-path-facing direction 215, such that the first imaging device 211 and the second imaging device 212 are optically aligned via the optical filter 217 to image the line.

As depicted, the respective optical axes 221, 222 of the first imaging device 111 and the second imaging device 112 are at about 90° to each other, and the optical filter is at about 45° to each of the respective optical axes 221, 222. Furthermore, the optical axis 221 of the first imaging device 211 is aligned with (and/or parallel to) the food-path-facing direction 215. Hence, in contrast to the optical filter 117, the optical filter 217 is further configured to: transmit the first wavelengths (e.g. of the first imaging device 211) from the line 206 to the first imaging device 211; and reflect the second wavelengths (e.g. of the second imaging device 212) from the line 209 to the second imaging device 212.

Hence, for example, as depicted, light 240 from the line 209 is received at the optical filter 217, and the optical filter 217: transmits light 241 of the first wavelengths to the first imaging device 211; and reflects light 242 of the second wavelengths to the second imaging device 212.

Figure 3:
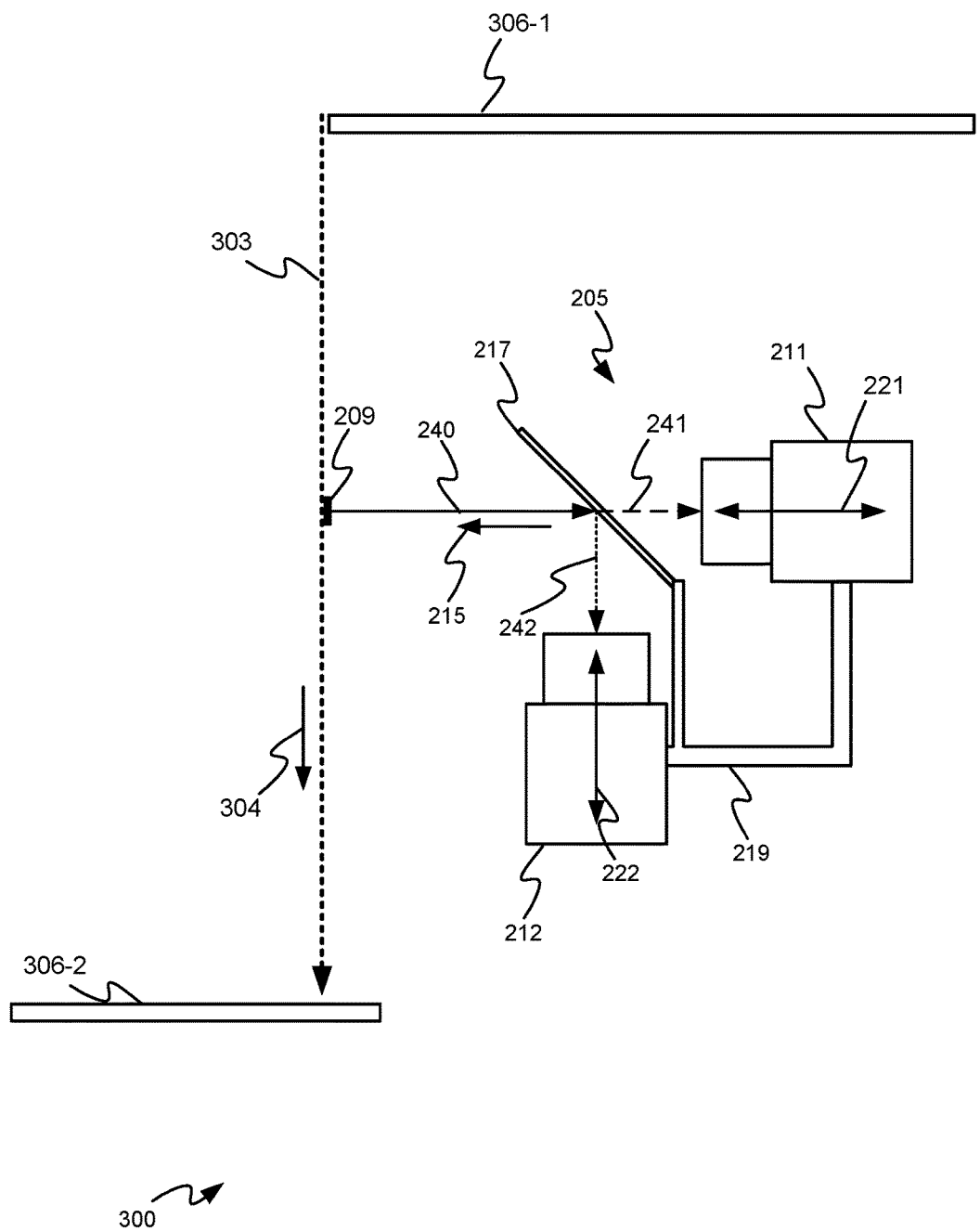
FIG. 3 depicts is a schematic view of a second optical configuration of a device for optically analyzing food products, according to non-limiting examples.

As mentioned above, the device 205 may be oriented in any suitable directions relative to a food product path. For example, attention is next directed to FIG. 3 which depicts a system 300 substantially similar to the system 200 with like components having like numbers. Specifically, the system 300 includes the device 205 but rotated at 90° relative to the system 200. For example, as depicted, the system 300 includes a waterfall food product path 303 in which food products fall along the waterfall food product path 303 in a food product path direction 304 from a first conveyor 306-1, located above the device 205, to a second conveyor 306-2, located below the device 205, the line 209 located at the waterfall food product path 303. In some examples, the device 205 may be located proximal the first conveyor 306-1 and/or closer to the first conveyor 306-1 than the second conveyor 306-2, to optically analyze the falling food products at a slower falling speed than would occur if the device 205 where located proximal the second conveyor 306-2 and/or closer to the second conveyor 306-2 than the first conveyor 306-1.

Regardless, the device 205 is generally oriented to optically analyze food products, as described above, as the food products fall along the waterfall food product path 303. As the imaging of the food products occur substantially simultaneously, at the same location (e.g. the line 209) using the imaging devices 211, 212 and the optical filter 217, the use of the device 205 in a waterfall configuration may be particularly useful as compared to systems where two separate imaging devices are used to optically analyze falling food products at different locations, as such data is particularly difficult to coordinate, as the food products accelerate while falling.

Figure 4:
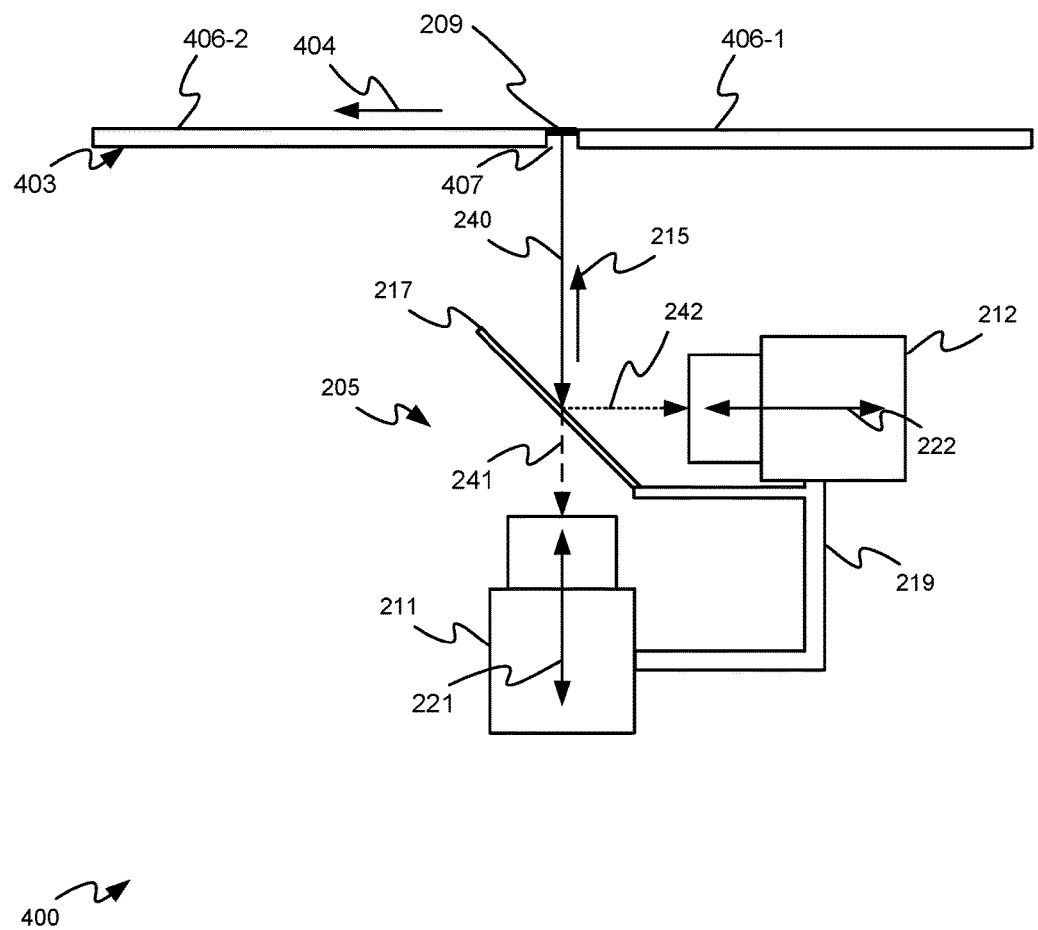
FIG. 4 depicts is a schematic view of a third optical configuration of a device for optically analyzing food products, according to non-limiting examples.

Attention is next directed to FIG. 4 which depicts a system 400 similar to the system 300 with like components having like numbers. Specifically, the system 400 includes the device 205 but rotated at 180° relative to the system 200. For example, as depicted, the system 300 includes a food product path 403 where food products are conveyed in a food product path direction 404, the food product path 403 comprising a first conveyor 406-1 and an adjacent second conveyor 406-2 with a gap 407 therebetween, the conveyors 406-1, 406-2 conveying the food products across the gap 407. Hence a size of the gap 407 may be compatible with the food products and/or the gap 407 may include an optically transparent window through which the device 205 optically analyzes the food products.

Regardless, the device 205 is generally located beneath the food product path 403 and oriented to optically analyze food products through the gap 407; hence, the line 209 is located at the gap 407.

As described above with respect to FIG. 1A, in some examples the device 105 includes a fold mirror, which may be removeable. Hence, attention is directed to FIG. 5 which depicts a schematic side view of a system 500 which is substantially similar to the system 100 with like components having like numbers, however in a "500" series rather than a "100" series.

The system 500 hence includes a food product path 503, where food products (not depicted) are conveyed in a food product path direction 504, and a device 505, similar to the device 105, for optically analyzing food products at a line 509 at the food product path 503. Indeed, the device 505 may represent one example of how the device 105 may be configured. While not depicted, the system 500 may include a lamp similar to the lamp 123 which illuminates the line 509, and a computing device similar to the computing device 130.

The device 505 is generally mounted relative to the food product path 503 along which food products are conveyed. The food product path 503 may comprise the conveyor 103 or another food product path, and the line 509 being imaged by the device 505, similar to the line 109, is located at the food product path 503, for example about perpendicular to the food product path 503 and/or the food product path direction 504. While only an end of the line 509 is depicted, the line 509 is understood to extend about perpendicularly across the food product path 503.

Figure 5:
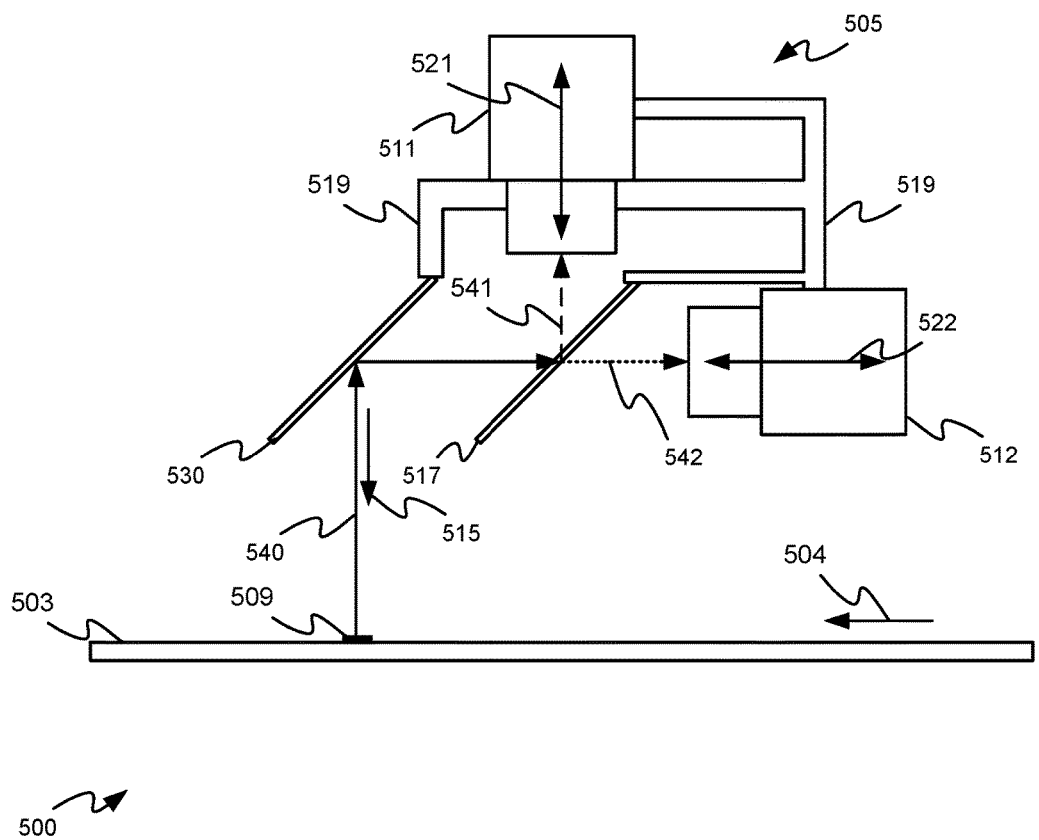
FIG. 5 depicts is a schematic view of a fourth optical configuration of a device for optically analyzing food products, according to non-limiting examples.

Furthermore, while in FIG. 5, the food product path 503 is depicted as "beneath" the device 505, the food product path 503 and the device 505 may be in any orientation relative to one another, similar to as described above. For example, the device 505 may be rotated by 90° to optically analyze food products on a waterfall food product path, similar to the orientation of the device 205 in FIG. 3 and/or the device 505 may be rotated by 180° to optically analyze food products from beneath, similar to the orientation of the device 205 in FIG. 4.

Similar to the device 105, the device 505 comprises: a first imaging device 511 sensitive to first wavelengths; a second imaging device 512 sensitive to second wavelengths, one of the first imaging device 511 and the second imaging device 512 comprising: a line-scan camera configured to acquire images of food products in a human-visible wavelength spectrum, at a line 509 in a food-path-facing direction 515, and an other of the first imaging device 511 and the second imaging device 512 comprising: a line-scan spectrometer configured to acquire spectroscopic images of the food products from the line in the food-path-facing direction 515; an optical filter 517 configured to: convey the first wavelengths from the line 509 to the first imaging device 511; and convey the second wavelengths from the line 509 to the second imaging device 512; and a frame 519 (depicted schematically) configured to align the optical filter 517 and respective optical axes 521, 522 of the first imaging device 511 and the second imaging device 512, relative to each other and the food-path-facing direction 515, such that the first imaging device 511 and the second imaging device 512 are optically aligned via the optical filter 517 to image the line.

However, in contrast to the device 205, but similar to the device 105, the device 105 further comprises a fold mirror 530. In particular, the frame 519 is further configured to: align the respective optical axes 521, 522 of the first imaging device 511 and the second imaging device 512 at about 90° to each other; align the optical filter 517 at about 45° to each of the respective optical axes 521, 522; and align the fold mirror 530 about parallel to the optical filter 517. The fold mirror 530 is generally positioned to: reflect the first wavelengths (e.g. of the first imaging device 511) and the second wavelengths (e.g. of the second imaging device 512) from the line 509 to the optical filter 517.

Hence, in contrast to the optical filter 217, the optical filter 517 is further configured to: reflect the first wavelengths from the fold mirror 530 to the first imaging device 511; and transmit the second wavelengths from the fold mirror 530 to the second imaging device 512. Hence, the optical filter 217 may comprise a hot mirror, while the optical filter 517 may comprise a cold mirror, depending on the configuration of the imaging devices 211, 212 and/or the imaging devices 511, 512.

Specifically, as depicted, light 540 from the line 509 is received at the fold mirror 530 and reflected to the optical filter 517; the optical filter 517: reflects light 541 of the first wavelengths to the first imaging device 511; and transmits light 542 of the second wavelengths to the second imaging device 512.

Furthermore, the food product path 503 may comprise a conveyor located in the food-path-facing direction 115 relative to both the respective optical axis 521 of the first imaging device 111 and the optical filter 517, the line 509 located at the conveyor about perpendicular thereto, similar to the orientation of the line 109 relative to the conveyor 103 of the system 100. Hence, in the system 500, the fold mirror 530 is positioned (e.g. by the frame 519) to reflect the first wavelengths and the second wavelengths at the conveyor to the optical filter 517 from the food-path-facing direction 515 towards the optical filter 517.

In some examples, the fold mirror 530 may be removeable, for example by detaching the fold mirror 530 from the frame 519 and removing the fold mirror 530 from the device 505. In these example, the device 505 may be used to optically analyze food products in one of two food-path-facing directions.

Figure 6:
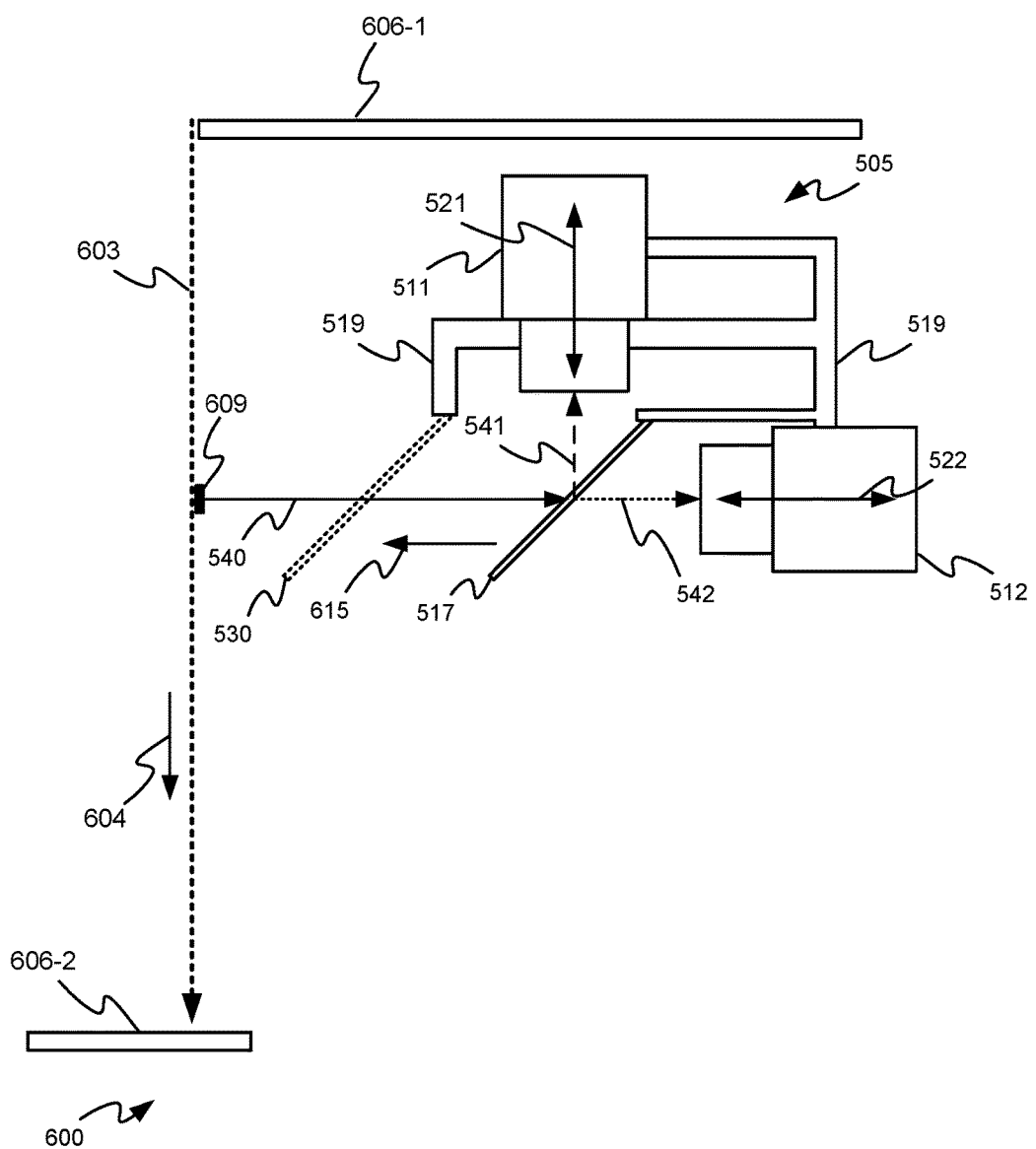
FIG. 6 depicts is a schematic view of a fifth optical configuration of a device for optically analyzing food products, according to non-limiting examples.

For example, attention is next directed to FIG. 6 which depicts the device 505 with the fold mirror 530 removed, though a location of the fold mirror 530, when present, is depicted in outline. In these examples, the device 505 may be used with a waterfall food product path 603, for example between two conveyors 606-1, 606-2, similar to the waterfall food product path 403, and the conveyors 406-1, 406-2. The waterfall food product path 603 is generally 90° to the food product path 503.

Hence, as depicted, when the removeable fold mirror 530 is removed, the device 505 optically analyzes food products at a line 609 in a food-path-facing direction 615 aligned with the optical axis 522 of the second imaging device 512, in contrast to when the removeable fold mirror 530 is present and the device 505 optically analyzes food products at the line 509 in the food-path-facing direction 515 aligned with the optical axis 521 of the first imaging device 511.

In particular, with reference to both FIG. 5 and FIG. 6, in some examples, the device 505 comprises the removeable fold mirror 520, and a food-path-facing direction includes one of: a first food-path-facing direction 515; or a second food-path-facing direction 615 about 90° to the first food-path-facing direction 515. When the removeable fold mirror 530 is present (as in FIG. 5), the removeable fold mirror 530 reflects the first wavelengths and the second wavelengths of the line 509 in the first food-path-facing direction 515 to the optical filter 517; and the optical filter 517 reflects the first wavelengths of the line 509 in the first food-path-facing direction 515 from the removeable fold mirror 530 to the first imaging device 511 and transmits the second wavelengths of the line 509 in the first food-path-facing direction 515 from the removeable fold mirror 530 to the second imaging device 512. However, when the removeable fold mirror 530 is removed (as in FIG. 6), the optical filter 517 reflects the first wavelengths of the line 609 in the second food-path-facing direction 615 to the first imaging device 511 and transmits the second wavelengths of the line 609 in the second food-path-facing direction 615 to the second imaging device 512.

Hence, the device 505 may be used with one of: a conveyor (e.g. the food product path 503) located in the first food-path-facing direction 515 aligned with the respective optical axis 521 of the first imaging device 211, the line 509 located at the conveyor about perpendicular thereto; and a waterfall food product path 603 in the second food-path-facing direction 615 aligned with the respective optical axis 522 of the second imaging device 512, the line 609 located at the waterfall food product path 604 about perpendicular thereto.

Indeed, a device that includes the device 505 (e.g. a device that includes the device 505 and the lamp 123 in a housing) may be adapted to include one or more a conveyor and a waterfall food product path.

In some examples, the device 505 maybe better adapted for a food product manufacturing environment and/or food product processing environment and/or food packaging environment using an enclosure. For example, attention is next directed to FIG. 7 which depicts a schematic view of the device 505 adapted to include an enclosure 701 configured to enclose the first imaging device 511, the second imaging device 512, the optical filter 517, the removeable fold mirror 530, and the frame 519. Hence, the enclosure 701 is depicted as enclosing the other components of the device 505.

The enclosure 701 is generally compatible with the optical analysis capabilities of the device 505 and hence enclosure 701 includes: a first aperture 711 located in the first food-path-facing direction 515; and a second aperture 712 located in the second food-path-facing direction 615. Hence, the imaging devices 511, 512 may be used to optically analyze food products through either of the apertures 711, 712 depending on whether the fold mirror 530 is present or not, as described above. In general, however, only one aperture 711, 712 may be used at a time.

As the enclosure 701 is generally provided to better adapt the device 505 for a food product manufacturing environment and/or food product processing environment and/or food packaging environment, each of the apertures 711, 712 are generally covered and the like, with at least one of the covers including a window through which optical analysis may occur. Indeed, in some examples, both of the apertures 711, 712 include a window through which optical analysis may occur.

However, in other examples, one of the first aperture 711 and the second aperture 712 is covered by a window transparent to the first wavelengths and the second wavelengths, and the other of the first aperture 711 and the second aperture 712 is covered by a cover that may or may not include a window.

Figure 7:
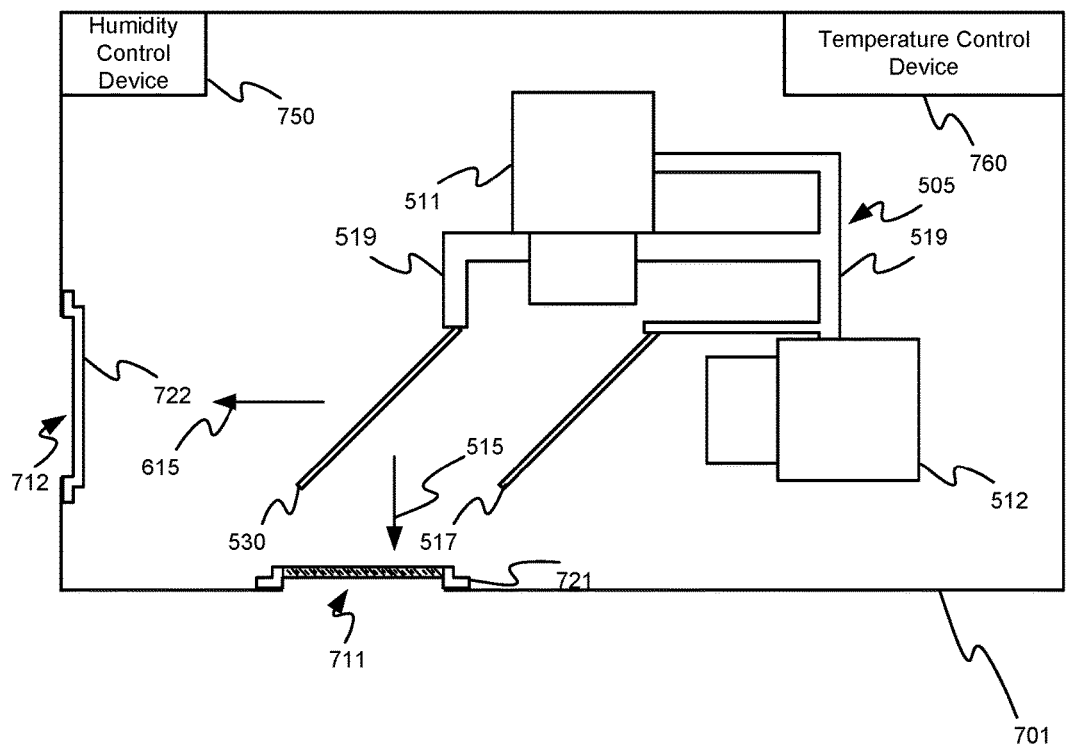
FIG. 7 depicts an enclosure for a device for optically analyzing food products, according to non-limiting examples.

For example, as depicted in FIG. 7, where the fold mirror 530 is present, and hence optical analysis occurs through the aperture 711, the aperture 711 is covered by a detachable window 721 (e.g. in a frame). The window 721 may be attached to the enclosure 701 using any suitable fastening device(s) such as bolts and the like (e.g. via bolt holes through a frame, and compatible holes and/or threaded holes at a wall of the enclosure 701 adjacent the aperture 711). As depicted, the window 721 is attachable to an interior wall of the enclosure 701, however the window 721 may alternatively be attachable to an exterior wall of the enclosure 701.

Similarly, in FIG. 7, the aperture 712 is covered by a cover 722 which may not be transparent to light. The cover 722 may be attached to the enclosure 701 using any suitable fastening device(s) such as bolts and the like (e.g. via bolt holes through a frame, and compatible holes and/or threaded holes at a wall of the enclosure 701 adjacent the aperture 712). As depicted, the cover 722 is attachable to an interior wall of the enclosure 701, however the window 721 may alternatively be attachable to an exterior wall of the enclosure 701.

Furthermore, the window 721 and the cover 722 may be swapped when the fold mirror 530 is removed such that optical analysis occurs through the aperture 712. Hence, each of the window 721 and the cover 722 may be removeable and attachable to either of the first aperture 711 and the second aperture 712. Alternatively, a detachable mirror may be provided at each of the apertures 711, 712.

In general, the enclosure 701 may comprise a box, and the like, which encloses the other components of the device 505. While not depicted, the box generally includes electrical connectors and/or electrical feedthroughs to connect the imaging devices 511, 512 to a computing device, such as the computing device 130, and a power source.

The box may include at least one removable wall and the like, for example to insert the other components of the device 505 and/or to remove or insert the fold mirror 530. It is further understood that the frame 519 is generally attached to the interior of the box. Any removeable walls and/or the detachable window 721 and the cover 722 are generally sealed when attached to the enclosure 701, such seals compatible with a food product manufacturing environment and/or food product processing environment and/or food packaging environment.

Indeed, the box of the enclosure 701 may be made from any material and/or materials compatible with a food product manufacturing environment and/or food product processing environment and/or food packaging environment. Hence, the enclosure 701 may be ruggedized with respect to temperature over a range of one or more of about 0.1° C. to about 60° C. and about 0.1° C. to about 100° C., which may be temperature ranges in use in a food product manufacturing environment and/or food product processing environment and/or food packaging environment. For example, food products may be processed and/or packaged at the low end of such temperature ranges, and external surfaces of the enclosure 701 may be cleaned at the high end of such temperature ranges. Hence, the enclosure 701 may be one or more of waterproof and resistant to disinfecting chemicals, for example used in cleaning the enclosure 701. Indeed, in general, the enclosure 701 is configured to protect components therein from water, disinfecting chemicals, and the like, and hence any seals and/or sealing material of the enclosure 701 are generally ruggedized to maintain seals over temperature ranges of one or more of about 0.1° C. to about 60° C. and about 0.1° C. to about 100° C.

Indeed, in some examples, as also depicted in FIG. 7, the device 505 may be adapted to include one or more of a humidity control device 750 and a temperature control device 760 located inside the enclosure 701. For example, the humidity control device 750 may include desiccants and the like, such that the enclosure 701 remains sealed, and such desiccants may be replaced periodically. However, in other examples, the humidity control device 750 may include a vent through one or more walls of the enclosure 701 through which humidity is vented, for example using a fan and the like. However, any suitable humidity control device is within the scope of present examples.

The temperature control device 760 may include one or more thermoelectric cooling (TEC) devices, attached to one or more an interior wall of the enclosure 701, such that heat from inside the enclosure 701 is radiated out of the enclosure 701 via one or more walls of the enclosure 701. However, any suitable temperature control device is within the scope of present examples.

In yet further examples, the device 205 may include an enclosure similar to the enclosure 701, however, in these examples, the second aperture 712 and the cover 722 may be optional.

Hence, present examples generally include an enclosure configured to enclose a first imaging device, a second imaging device, an optical filter, and a frame, the enclosure including a window transparent to the first wavelengths (e.g. of a first imaging device) and the second wavelengths (e.g. of a first imaging device), the window positioned in the enclosure to convey the first wavelengths and the second wavelengths of a line being imaged to the optical filter. Such an enclosure may be ruggedized with respect to temperature over a range of one or more of about 0.1° C. to about 60° C. and about 0.1° C. to about 100° C. Further, such an enclosure may be one or more of waterproof and resistant to disinfecting chemicals. Further, such an enclosure may further comprise one or more of a humidity control device and a temperature control device located inside the enclosure.

Figure 8:
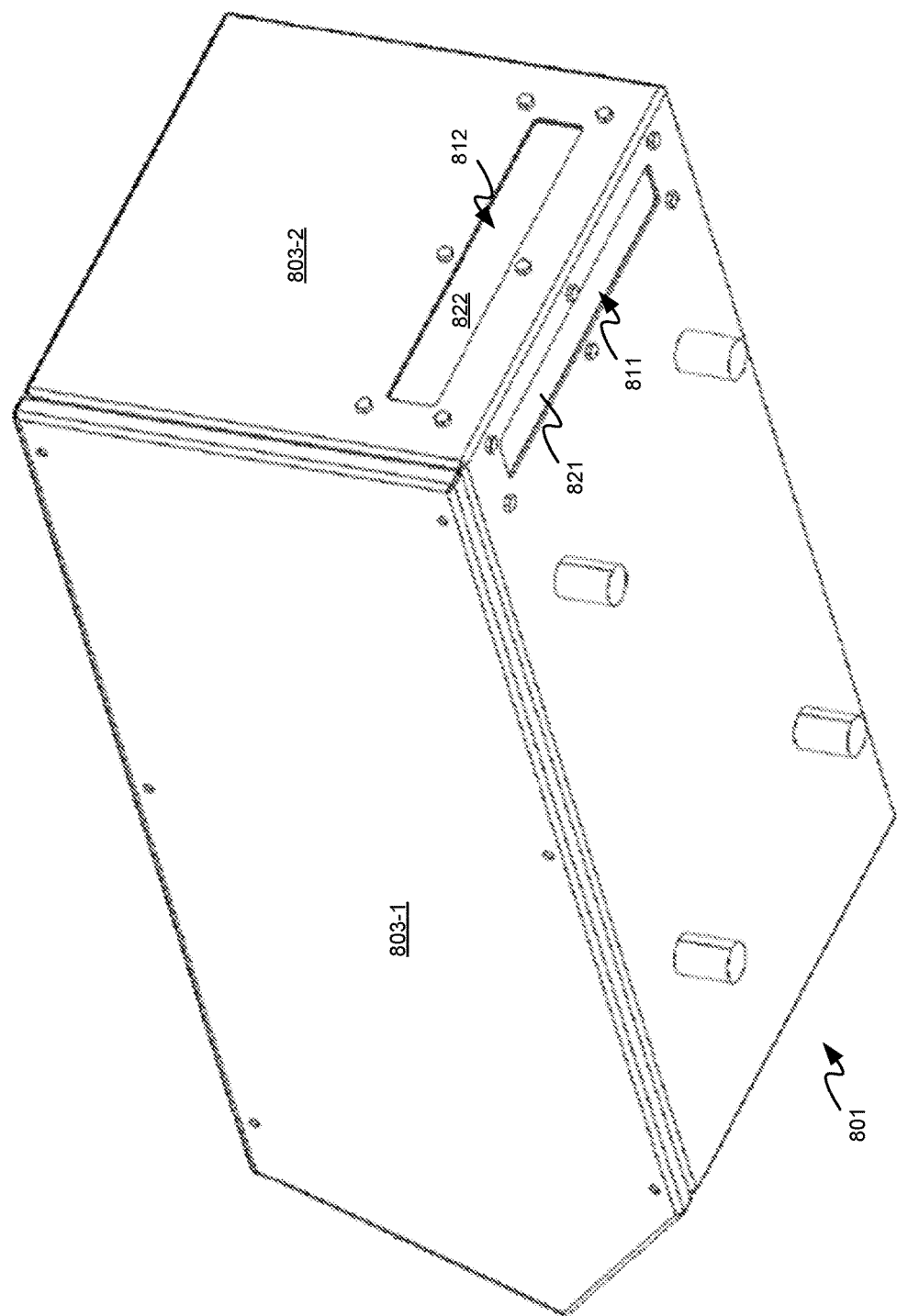
FIG. 8 depicts an enclosure for the device of FIG. 1A, according to non-limiting examples.

Attention is next directed to FIG. 8 which depicts an example enclosure 801, similar to the enclosure 701, however the enclosure 801 is specifically configured for incorporation with the device 105 and is of dimensions suitable for the enclosing the other components of the device 105. While not depicted, the enclosure 701 (with the device 105 inside) and the lamp 123 may be mounted relative to each other and the conveyor 103 using a support structure in a housing.

The example enclosure 801 includes two removeable walls 803-1, 803-2, and two apertures 811, 812, each of the apertures 811, 812 respectively corresponding to the apertures 711, 712. Hence, the aperture 811 is located for use with the device 105 configured as depicted in FIG. 1A, with the fold mirror 131 in use; hence the aperture 811 has dimensions suitable for imaging at the line 109. As in FIG. 1A, the conveyor 103 is located beneath the device 105, the aperture 811 of the enclosure 801 may be located through a bottom wall of the enclosure 801. The aperture 812 is located for use with the device 105 with the fold mirror 131 removed, similar to the configuration of the device 505 in FIG. 6; hence, the aperture 812 may be located through a front wall (e.g. the removeable wall 803-2) of the enclosure 801 that is perpendicular to the bottom wall where the aperture 811 is located. Hence, each of the apertures 811, 812 have dimensions suitable for imaging at a line similar to the line 109 and/or the line 609. As depicted, the aperture 811 is covered by window 821 (similar to the window 721), and the aperture 812 is covered by cover 822, similar to the cover 722; the window 821 and the cover 822 are attached to the enclosure 801 via bolts and the like. Similarly, each of the removeable walls 803-1, 803-2 may be attached to the enclosure 801 via bolts and the like.

Figure 9:
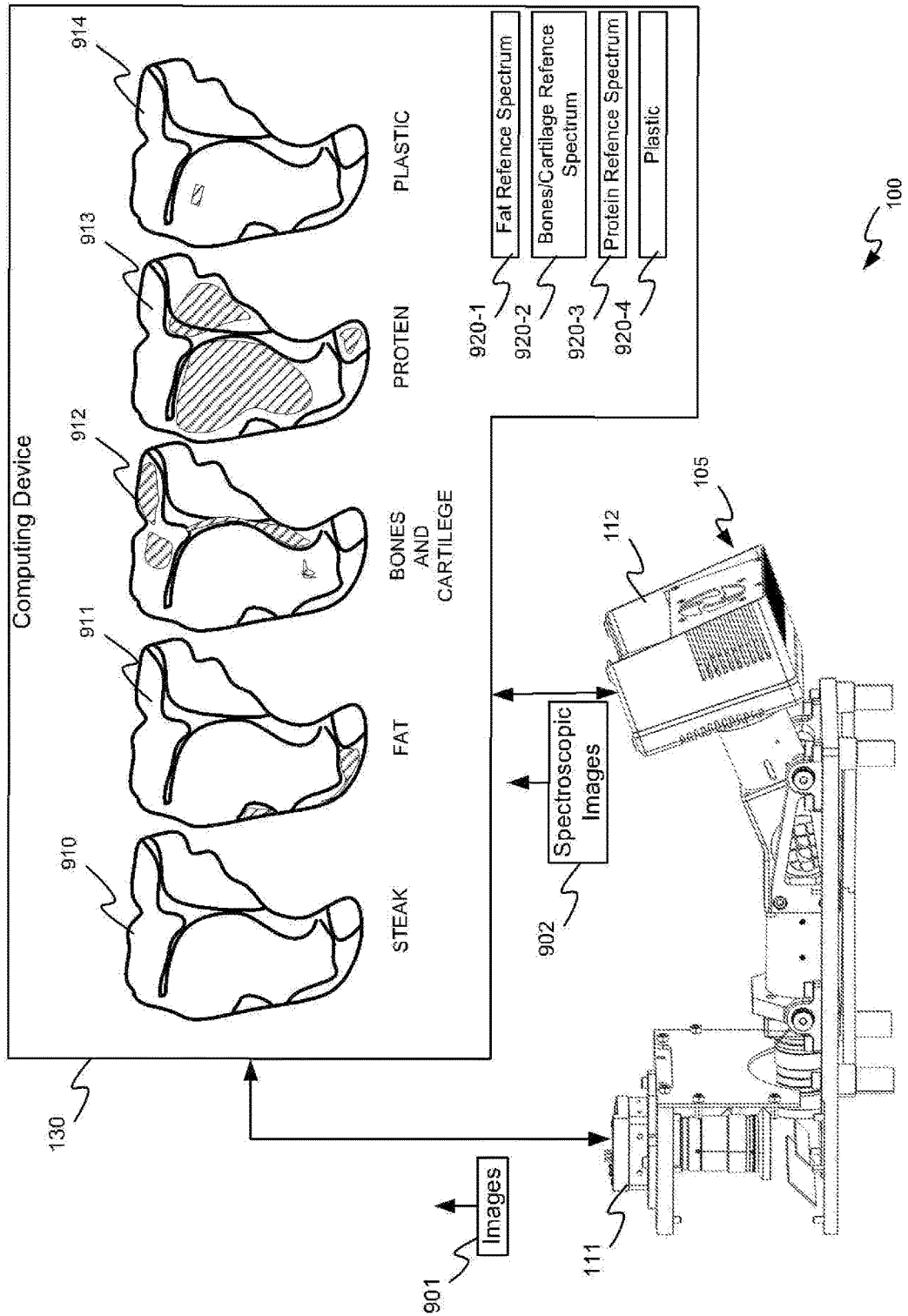
FIG. 9 depicts a computing device, of the system of FIG. 1A, analyzing line-scan images and spectroscopic images to determine quality of food products, according to non-limiting examples.

Attention is next directed to FIG. 9, which depicts a portion of system 100, and in particular the device 105 and the computing device 130. While not all components of the system 100, there are nonetheless understood to be present. In particular, FIG. 9 depicts the device 105 transmitting images 901 (e.g. line-scan images of the food products 101 at the line 109), from the first imaging device 111 to the computing device 130, and transmitting spectroscopic images 902 (e.g. spectroscopic line-scan images of the food products 101 at the line 109), from the second imaging device 112 to the computing device 130. The images 901 and the spectroscopic images 902 are generally acquired simultaneously at the line 109, as described above, and hence information in each of the images 901 and the spectroscopic images 902 acquired simultaneously may be easily coordinated by the computing device 130.

Hence, for example, when one of the food products 101 comprises a steak, the computing device 130 may merge the images 901 to form an image 910 of the steak; and the computing device 130 may use the spectroscopic images 902 to locate different food product types and/or impurities in the images 901 and/or the image 910. For example, the computing device 130 may store (e.g. in a memory), and/or have access to, reference spectra for various food product types and/or impurities; as depicted, the computing device 130 stores a reference spectrum 920-1 for fat, a reference spectrum 920-2 for bones and/or cartilage, a reference spectrum 920-3 for protein, and a reference spectrum 920-4 for plastic (the reference spectra 920-1, 920-2, 920-3, 920-4 interchangeably referred to hereafter, collectively, as reference spectra 920 and, generically, as a reference spectrum 920). Hence, the computing device 130 may compare each line segment of the spectroscopic images 902 with the reference spectra 920 to determine locations in the steak of, for example, fat, bones/cartilage, protein and plastic. The locations of fat, bones/cartilage, protein and plastic may then be located in the image 910.

For example, as depicted, the computing device 130 generates an image 911, from the image 910, the spectroscopic images 902 and the reference spectrum 920-1 to show locations of fat in the steak (e.g. the locations of fat corresponding to the hatched regions in the image 911). Similarly, as depicted, the computing device 130 generates an image 912, from the image 910, the spectroscopic images 902 and the reference spectrum 920-2 to show locations of bones and cartilage in the steak (e.g. the locations of bones and cartilage corresponding to the hatched regions in the image 912). Similarly, as depicted, the computing device 130 generates an image 913, from the image 910, the spectroscopic images 902 and the reference spectrum 920-3 to show locations of protein in the steak (e.g. the locations of protein corresponding to the hatched regions in the image 913). Similarly, as depicted, the computing device 130 generates an image 914, from the image 910, the spectroscopic images 902 and the reference spectrum 920-4 to show locations of plastic impurities and/or contaminants in the steak (e.g. a location of plastic corresponding to the hatched regions in the image 914).

However, the images 901, 911, 912, 913, 914 need not be generated; rather, the computing device 130 may alternatively generate a notification (e.g. using a display screen, a speaker, lights, and or other types of notification devices) of an impurity and/or a contaminant in a food product being optically analyzed, and/or a notification of impurity and/or a contaminant type, and/or a notification of fat content and/or a notification of fat marbling, and the like.

Details of the lamp 123 for illuminating food products at a line are now described. In particular, the lamp 123 is adapted for use in a product manufacturing environment and/or food product processing environment and/or food packaging environment, and the like. Indeed, such environments may have rigorous standards that have to be followed. For example, many lamps include a glass window covering an aperture, and such standards may indicate that food products in such an environment have to be protected from shattered glass.

Figure 10:
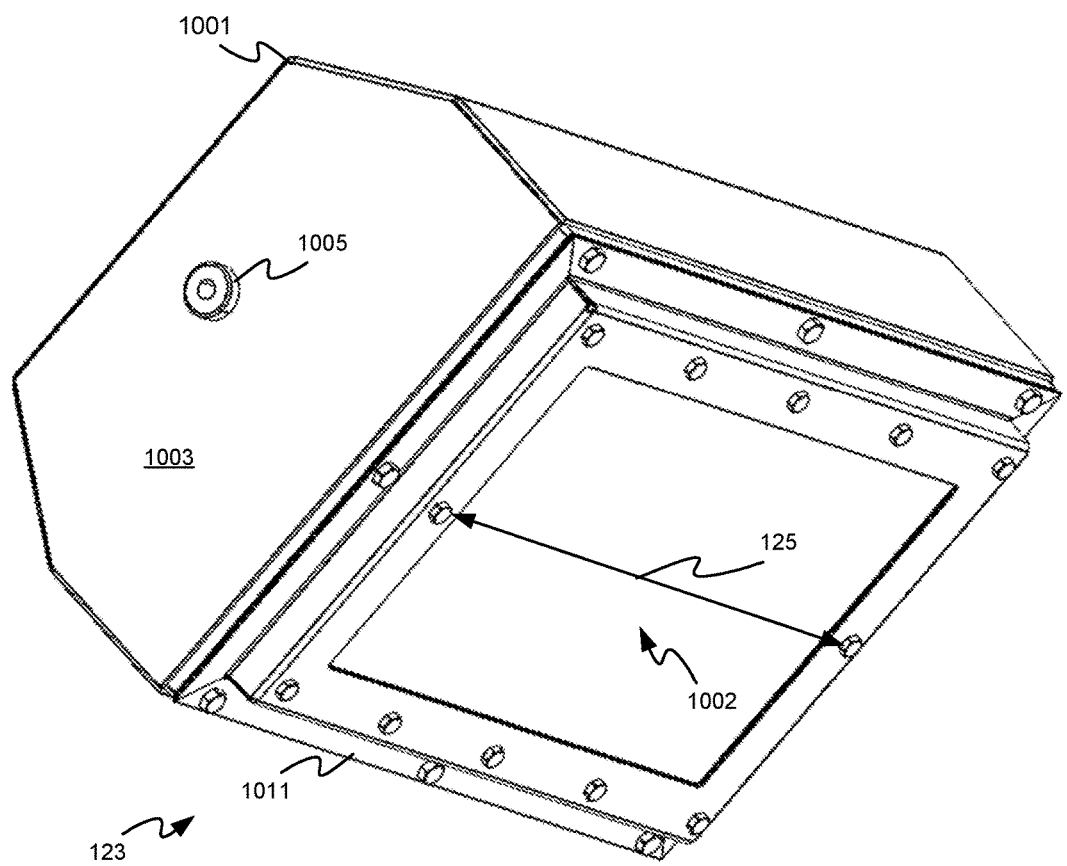
FIG. 10 depicts a perspective view of lamp for illuminating food products along a line, according to non-limiting examples.
Figure 11:
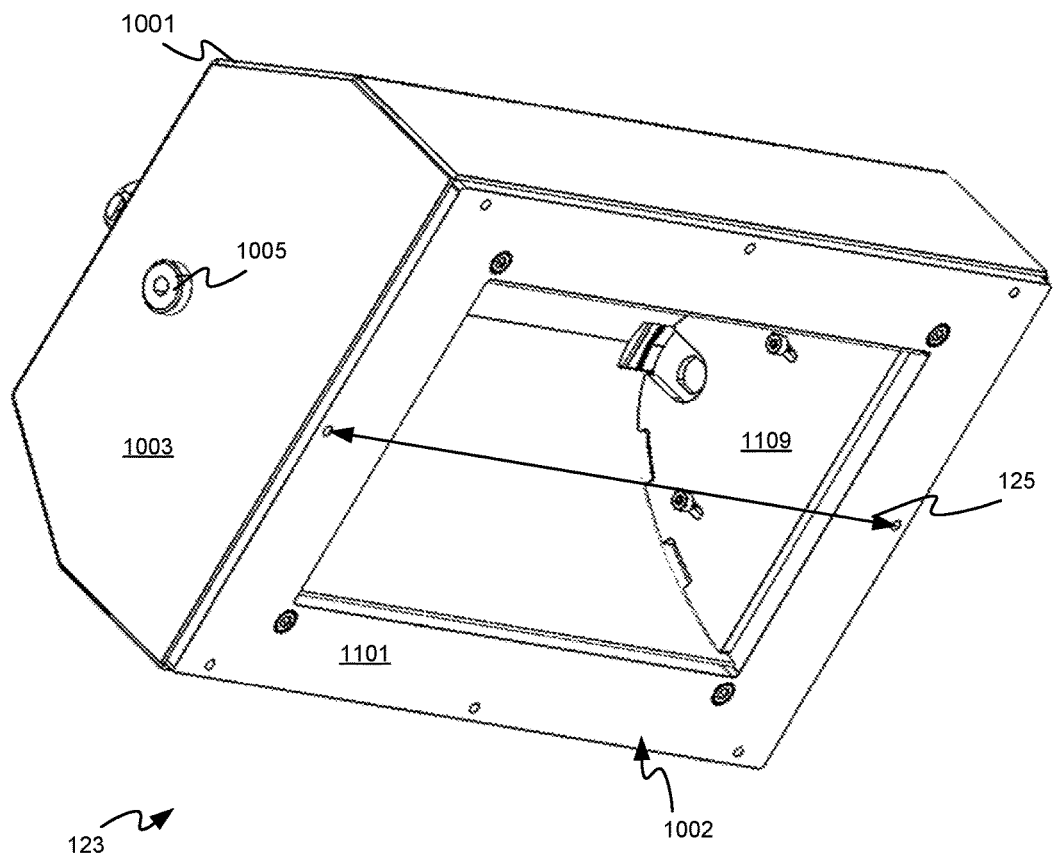
FIG. 11 depicts a perspective view of the lamp of FIG. 10 with a removeable frame removed, according to non-limiting examples.

Attention is next directed to FIG. 10 and FIG. 11, each of which depicts a perspective view of the lamp 123, which includes a housing 1001 and a light emitting side 1002 (e.g. through which light is emitted), with a length longer than a width (e.g. the light emitting side 1002 may be rectangular). Hence, the housing 1001 and/or the light emitting side 1002 and/or the lamp 123, in general, are each arranged along the longitudinal axis 125. The housing 1001 may be a unified housing or, as depicted, include various sections and/or panels, including a side panel 1003, as well as mounting fixtures 1005 for mounting the lamp 123 for example in a housing, and the like, relative to the device 105 and the conveyor 103, as depicted in FIG. 1. The sections of the housing 1001 may be fastened together using any suitable fasteners.

The lamp 123 further comprises a removeable frame 1011 attached to the housing 1001, for example around an opening of the housing (described below). In particular, FIG. 10 depicts the lamp 123 with the removeable frame 1011 attached to a frame mating plate 1101 of the housing 1001 (e.g. using fasteners such as bolts, clamps, and the like), and FIG. 11 depicts the lamp 123 with the removeable frame 1011 removed from the frame mating plate 1101 of the housing 1001.

Details of components of the removeable frame 1011 are described in further detail below with respect to FIG. 16 and FIG. 17.

Figure 12:
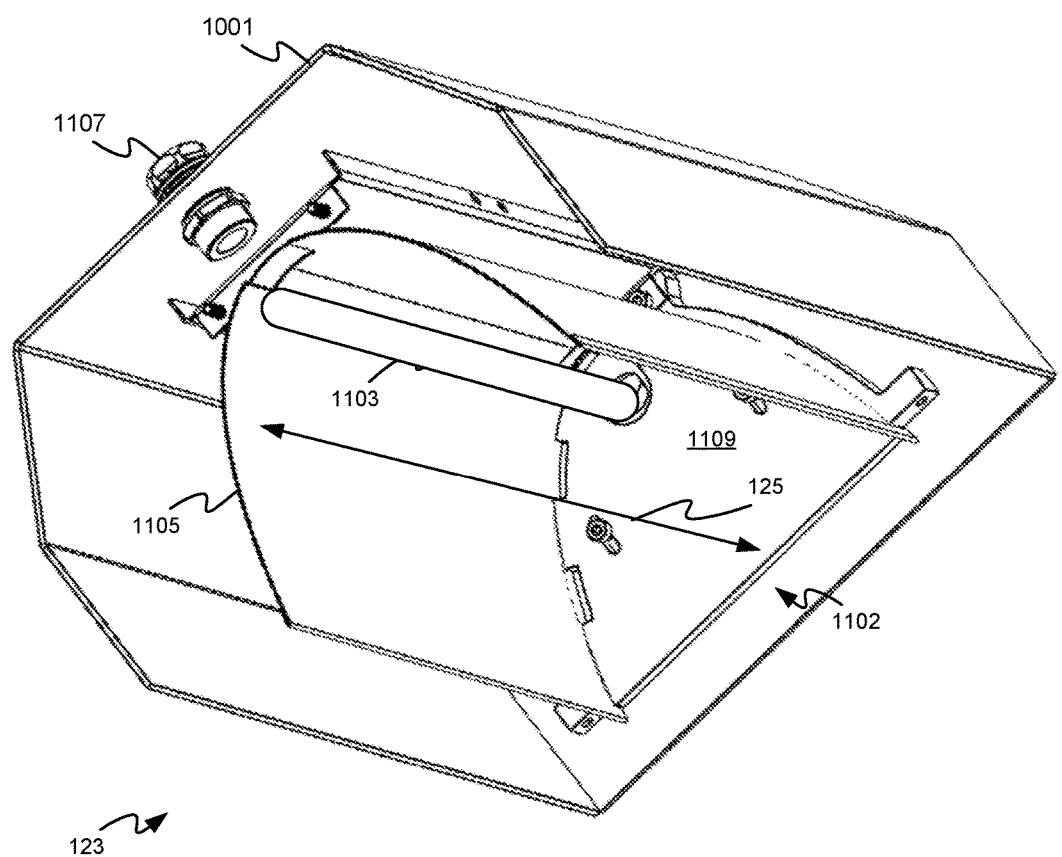
FIG. 12 depicts a perspective view of the lamp of FIG. 10 with some components removed to show an interior of the lamp, according to non-limiting examples.
Figure 13:
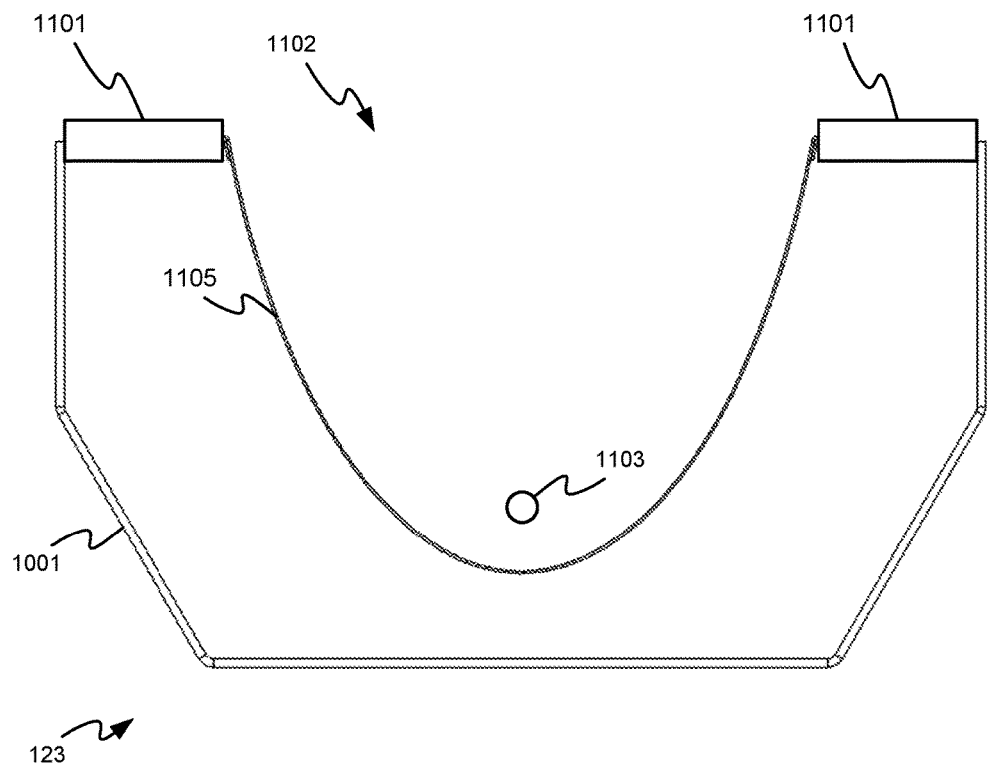
FIG. 13 depicts a schematic cross-section of the lamp of FIG. 10 through a plane perpendicular to a longitudinal axis, according to non-limiting examples.

However, attention is next directed to FIG. 12, which depicts a portion of the lamp 123, with the side panel 1003, the removeable frame 1011 and the frame mating plate 1101 removed, to show interior components of the lamp 123, and FIG. 13 which depicts a schematic cross section of the lamp 123 through a plane perpendicular to the longitudinal axis 125.

As depicted in FIG. 12 and FIG. 13, the lamp 123 comprises: the housing 1001 having the longitudinal axis 125 and an opening 1102 along the longitudinal axis 125; a light source 1103 located in the housing 1001 along the longitudinal axis 125; and a reflector 1105 positioned in the housing 1001 along the longitudinal axis, the reflector 1105 to reflect light from the light source 1103 through the opening 1102 and focus the light at a line (e.g. the line 109). The opening 1102 may generally be defined by one or more of an aperture through the frame mating plate 1101, and the length and width of the reflector 1105 at the light emitting side 1002 of the housing 1001.

While electrical connectors to the light source 1103 are not depicted, they are nonetheless understood to be present and, with reference to FIG. 12, the lamp 123 may further comprise at least one electrical feedthrough 1107 for connecting electrical connectors of the light source 1103 to an external power source. The at least one electrical feedthrough 1107 may be airtight and/or watertight.

Furthermore, as best seen in FIG. 12, the lamp 123 may include opposing interior reflector side panels 1109 (e.g. at ends of the reflector 1105), though only one interior reflector side panel 1109 is depicted in FIG. 12, with the opposing interior reflector side panel 1109 removed to better show the light source 1103 and the reflector 1105.

In the depicted examples, as best seen in FIG. 13, the reflector 1105 may be elliptical in a cross-section perpendicular to the longitudinal axis 125, and, as best seen in FIG. 12, the reflector 1105 is generally elongated along the longitudinal axis 125. However, the reflector 1105 may alternatively be parabolic in cross-section and/or any other shape which focuses light from the light source 1103 along a line through the opening 1102.

The light source 1103 may hence also be elongated along the longitudinal axis 125, with the light source 1103 being located at a focal point and/or an elliptical focal point, and the like, of the reflector 1105. The light source 1103 may comprise a halogen light source and/or a halogen light bulb, and is generally removeable and/or replaceable (e.g. in FIG. 11, the light source 1103 is absent). Hence, the lamp 123 may generally include a receptacle for receiving the light source 1103.

Figure 14:
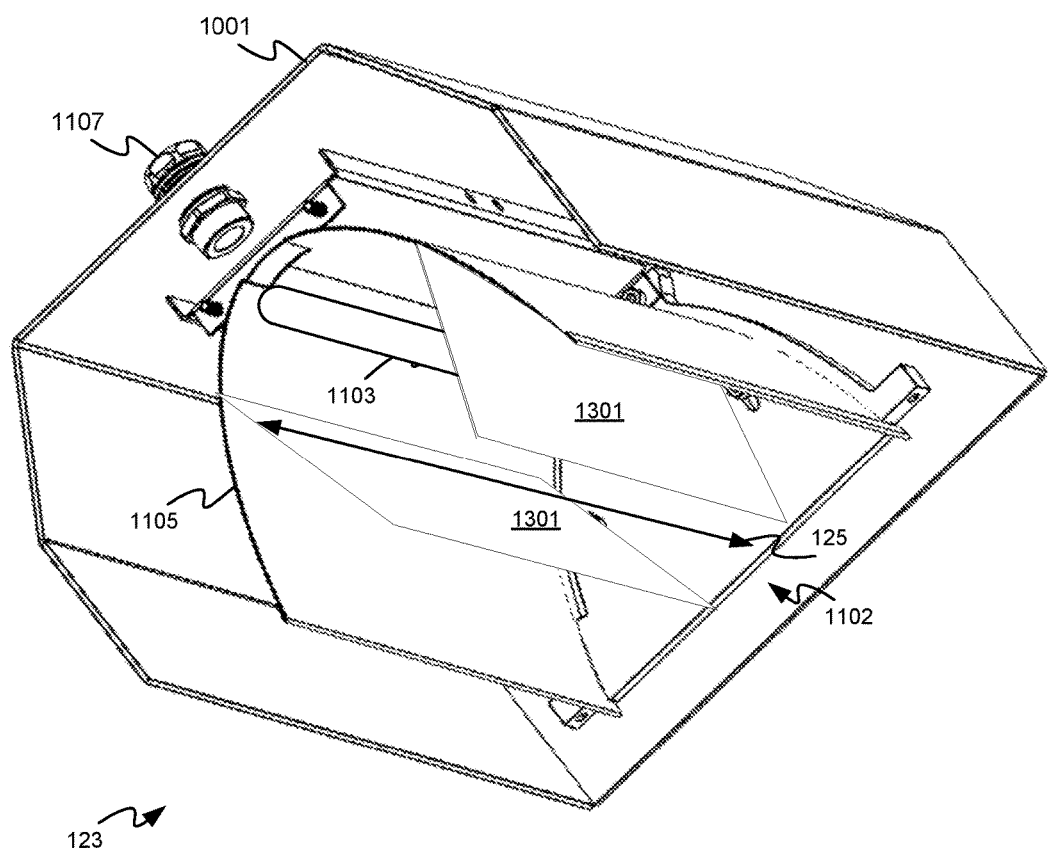
FIG. 14 depicts a perspective view of the lamp of FIG. 10 adapted to include two sheets of diffusing material, according to non-limiting examples.
Figure 15:
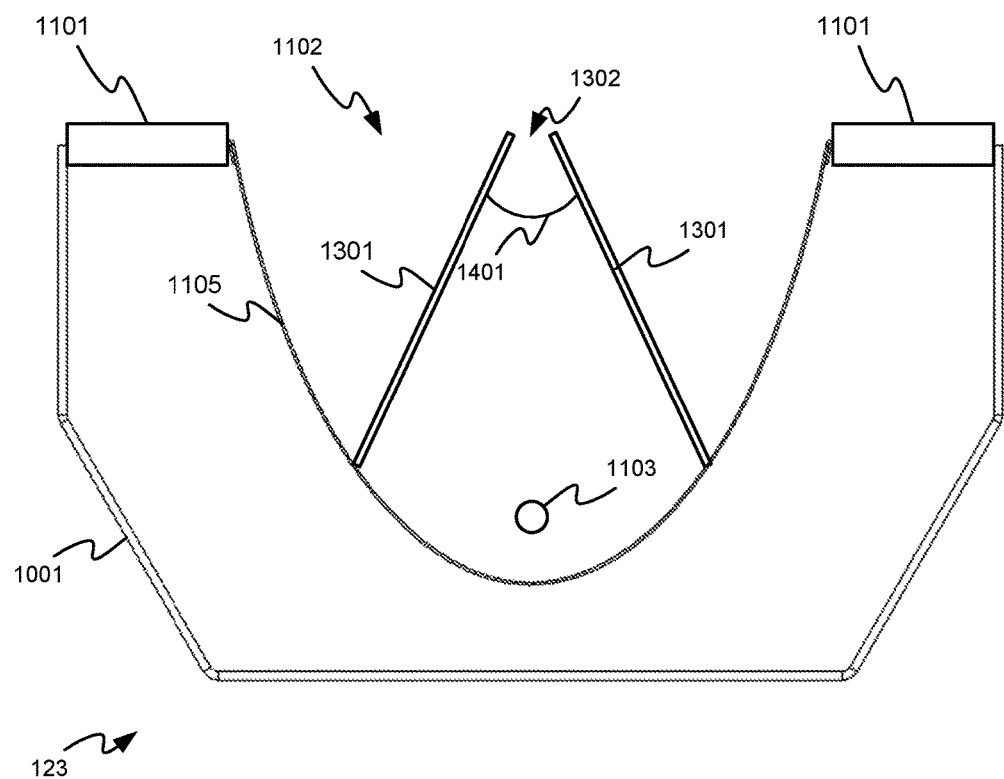
FIG. 15 depicts a schematic cross-section of the lamp of FIG. 10 adapted to include two sheets of diffusing material, the cross-section through a plane perpendicular to a longitudinal axis, according to non-limiting examples.

Attention is next directed to FIG. 14 and FIG. 15, which are substantially similar to FIG. 12 and FIG. 13, respectively, with like components having like numbers. However, in FIG. 14 and FIG. 15, the lamp 123 has been adapted to include two sheets 1301 of diffusing material located in the housing 1001 along the longitudinal axis 125, the two sheets 1301 of diffusing material extending from the reflector 1105 towards the opening 1102 on either side of the light source 1103, forming an angle 1401 with each other and being closer together at the opening 1102 than towards the light source 1103, forming an opening 1302 narrower than the opening 1102. While the two sheets 1301 may include any suitable diffusing material compatible with the lamp environment (e.g. compatible with any heat output by the light source 1103), in some examples, each of the two sheets 1301 of diffusing material may a respective polytetrafluoroethylene (PTFE) sheet.

The two sheets 1301 of diffusing material generally diffuse light from the light source 1103, which is focused by the reflector 1105 through the opening 1302, and assist in more uniformly illuminating the line 109 and/or any area that the lamp 123 is illuminating. Hence, the opening 1302 formed by the two sheets 1301 of diffusing material may better define the area 129 for illuminating the food products 101, for example (with reference to FIG. 1), by narrowing the area 129 and/or by more uniformly illuminating the area 129, the line 109 being in the area 129. Indeed, as described above, the device 105 and the lamp 123 are aligned such that the line 109 is within the area 129.

While not depicted in FIG. 14 and FIG. 15, it is understood that the lamp 123 may further include one or more holders (e.g. at the interior reflector side panels 1109) for holding the two sheets 1301 of diffusing material in position.

Figure 16:
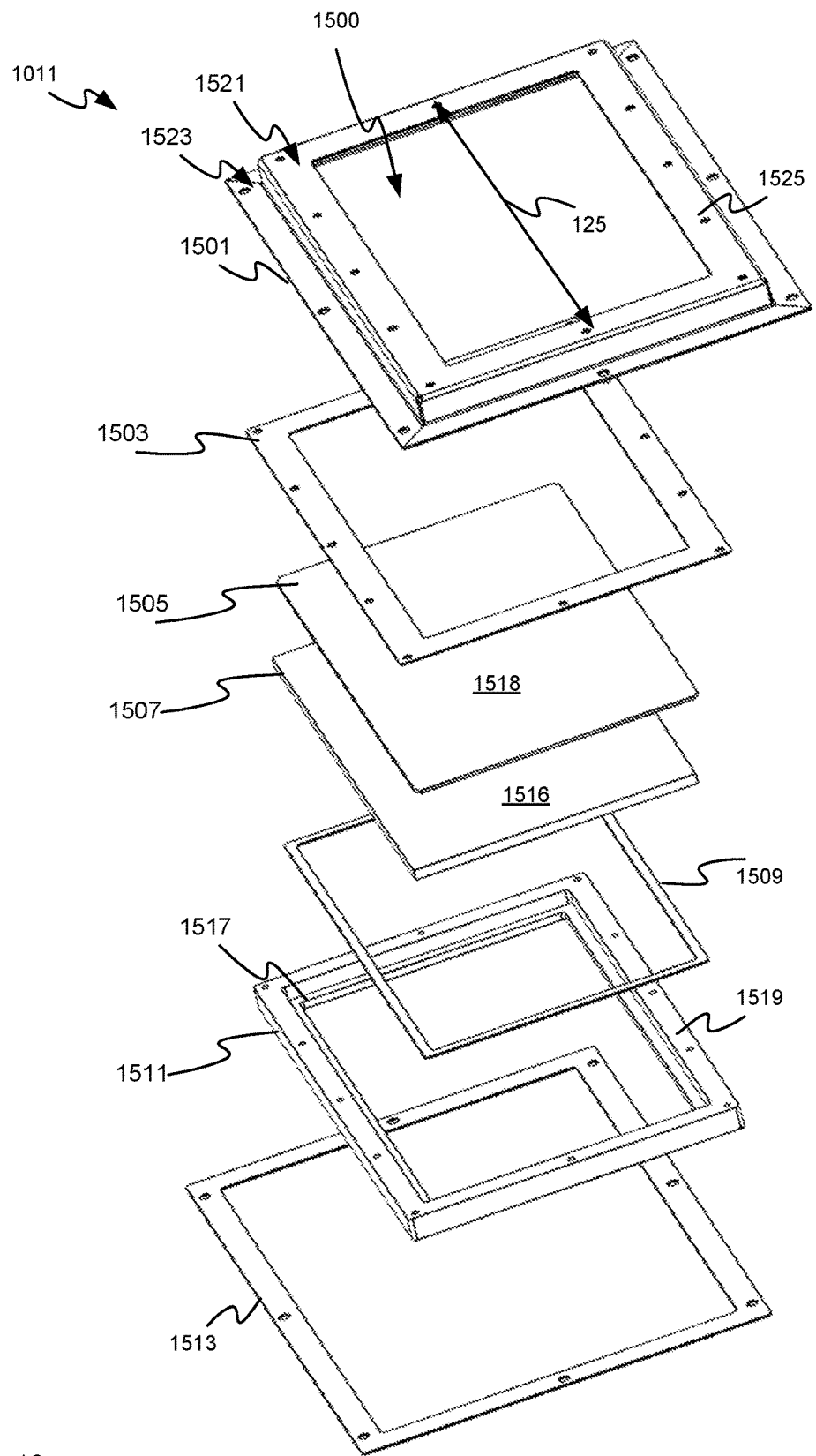
FIG. 16 depicts an exploded perspective view of a removeable frame of the lamp of FIG. 10, according to non-limiting examples.
Figure 17:
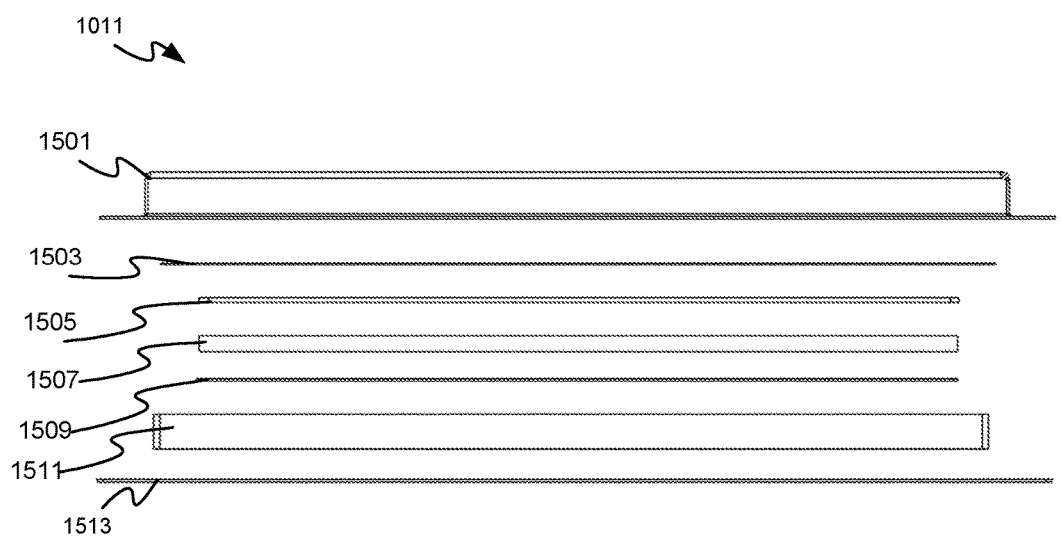
FIG. 17 depicts an exploded side view of a removeable frame of the lamp of FIG. 10, according to non-limiting examples

Attention is next directed to FIG. 16 and FIG. 17, each of which depicts an exploded view of the removeable frame 1011. In particular, FIG. 16 depicts a perspective exploded view of the removeable frame 1011, with the orientation of the removeable frame 1011 in FIG. 16 indicated via the longitudinal axis 125. FIG. 17 depicts a side exploded view of the removeable frame 1011.

The removeable frame 1011 generally includes an aperture 1500 therethrough which is aligned with the opening 1102 of the housing 1001 along the longitudinal axis 125 when the removeable frame 1011 is attached to the housing 1001. Hence the aperture 1500 generally provides a path through which light from the light source 1103 exits the lamp 123. Hence, the dimensions of the aperture 1500 are generally compatible with illuminating the area 129 and the aperture 1500 (as depicted) may be generally rectangular.

In the depicted example, the removeable frame 1011 comprises, from front to back (the back of the removeable frame 1011 mating with the frame mating plate 1101 when attached to the housing 1001, and the front of the removeable frame 1011 located at the light emitting side of the lamp 123 when the removeable frame 1011 is attached to the housing 1001): a bezel 1501; a front sealing member 1503; a transparent polymer film 1505; a glass window 1507; a rear sealing member 1509; and a glass mating plate 1511. Also depicted is a frame mating seal 1513 used to provide a seal between the removeable frame 1011 and the frame mating plate 1101.

Furthermore, there are respective apertures through each of the bezel 1501, the front sealing member 1503, the rear sealing member 1509, a glass mating plate 1511, and the frame mating seal 1513. The respective apertures all form the aperture 1500, and may all be of similar size and dimensions.

However, the glass window 1507 is generally located in the aperture 1500, and the transparent polymer film 1505 is generally located at an outward facing side 1516 of the glass window 1507, each of the glass window 1507 and the transparent polymer film 1505 extending into the removeable frame 1011 past a perimeter of the aperture 1500. As will also be explained hereafter, there is also seal between the transparent polymer film 1505 and the perimeter of the aperture 1500. In some examples, the transparent polymer film 1505 may reside at the outward facing side 1516 of the glass window 1507 without being bonded thereto (e.g. and held in place via friction). However, in other examples, the transparent polymer film 1505 may be bonded to the outward facing side 1516 of the glass window 1507 using a suitable optical epoxy, heat bonding, and/or any other suitable bonding process.

For example, as depicted, the glass mating plate 1511 includes a shelf 1517 around a perimeter of an interior wall of the glass mating plate 1511, the exterior perimeter of the shelf 1517 being larger than the perimeter of the aperture 1500, and the shelf 1517 facing outward. The rear sealing member 1509 resides against the shelf 1517, the glass window 1507 resides against the rear sealing member 1509 (such that the rear sealing member 1509 resides around the perimeter of an inward facing side of the glass window 1507), the transparent polymer film 1505 resides against the outward facing side 1516 of the glass window 1507, and the front sealing member 1503 resides around the perimeter of an outward facing side 1518 of the transparent polymer film 1505. As depicted, the front sealing member 1503 is of larger dimensions than the transparent polymer film 1505 such that a perimeter of the front sealing member 1503 resides around a perimeter of a front surface 1519 of the glass mating plate 1511.

As depicted, the bezel 1501 generally comprises a chassis 1521 and a lip 1523 extending about perpendicularly around a perimeter of the chassis 1521, for example from a rear edge of a side wall of the chassis 1521. The chassis 1521 is generally of a size and shape to receive, therein, the front sealing member 1503, and the glass mating plate 1511, with the transparent polymer film 1505, the glass window 1507, and the rear sealing member 1509 in the glass mating plate 1511. When the front sealing member 1503, and the glass mating plate 1511 are received in the chassis 1521, the front sealing member 1503 resides against an interior of a front face 1525 of the chassis 1521. The chassis 1521 and the glass mating plate 1511 each include complementary holes through which fasteners, such as bolts, and the like, may be inserted, to fasten the glass mating plate 1511 to the bezel 1501, and apply pressure to the rear sealing member 1509 and the front sealing member 1503. However, any suitable fasteners may be used including, but not limited to, clamps, and the like.

Such pressure provides a seal between the transparent polymer film 1505 and the perimeter of the aperture 1500 (e.g. via the front sealing member 1503 against the interior of the chassis 1521), as well as a seal between the glass window 1507 and the perimeter of the aperture 1500 (e.g. via the rear sealing member 1509 against the shelf 1517 of the glass mating plate 1511).

Hence, the removeable frame 1011 may be assembled by attaching the bezel 1501 to the glass mating plate 1511 with the transparent polymer film 1505 and the glass window 1507 covering the aperture 1500, and the sealing members 1503, 1509 used to seal the transparent polymer film 1505 and the glass window 1507 in the removeable frame 1011. Indeed, the bezel 1501 and the glass mating plate 1511, together, comprise a structure to attach the glass window 1507 and the transparent polymer film 1505 to the removeable frame 1011.

Furthermore, the removeable frame 1011 may be attached to the frame mating plate 1101 via complementary holes in the lip 1523 of bezel 1501 and the glass mating plate 1511, through which fasteners, such as bolts, and the like, may be inserted. However, any suitable fasteners may be used including, but not limited to, clamps, and the like. Furthermore, the frame mating seal 1513 is generally located between the lip 1523 of bezel 1501 and the glass mating plate 1511, providing a seal between the removeable frame 1011 and the frame mating plate 1101.

Hence, the seal between the transparent polymer film 1505 and the perimeter of the aperture 1500 (e.g. via the front sealing member 1503) is at a front facing side of the removeable frame 1011 such that if the glass window 1507 (or the light source 1103) breaks when the removeable frame 1011 is attached to the housing 1001 of the lamp 123, the shattered glass will be contained in the housing 1001 via the seal between the transparent polymer film 1505 and the perimeter of the aperture 1500$h$, and the seal between the removeable frame 1011 and the frame mating plate 1101.

For example, each of the glass window 1507 and the transparent polymer film 1505 extend past the aperture 1500 into the removeable frame 1011 (e.g. onto the shelf 1517), and the dimensions of each of the glass window 1507 and the transparent polymer film 1505 are generally larger than respective dimensions of the aperture 1500; for example, as depicted the aperture 1500 is a rectangle, and each of the glass window 1507 and the transparent polymer film 1505 are also rectangles larger than the rectangle of the aperture 1500. Hence, any shattered glass is contained within the lamp 123.

A material for the transparent polymer film 1505 is generally selected to be tear resistant (e.g. when in contact with shattered glass) and transparent to light emitted by the light source 1103 (and in particular the first wavelengths to which the first imaging device 111 is sensitive, and the second wavelengths to which the second imaging device 112 is sensitive). Furthermore, the transparent polymer film 1505 is generally compatible with the heat generated by the light source 1103. In a successful prototype the transparent polymer film 1505 comprises fluorinated ethylene propylene (FEP), though other suitable polymers are within the scope of present examples.

As mentioned previously, the lamp 123 is generally configured for use in a food product manufacturing environment and/or food product processing environment and/or food packaging environment. Hence, at least the housing 1001, the removeable frame 1011 and the various seals described above may be one or more of airtight and watertight.

Figure 18:
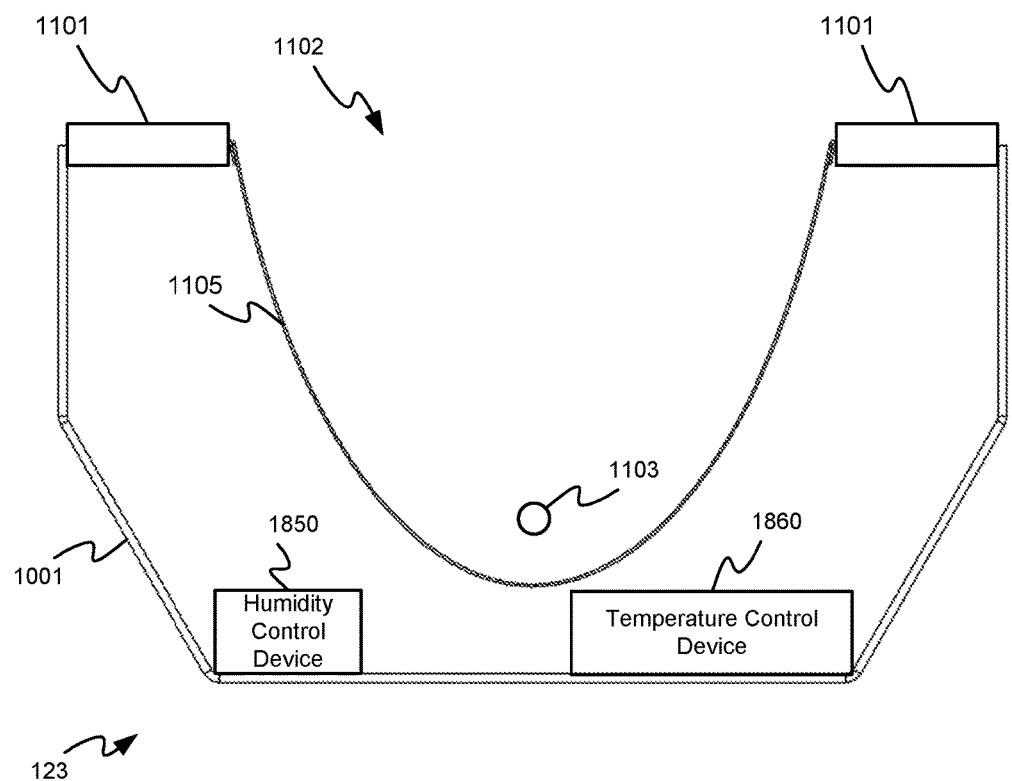
FIG. 18 depicts a schematic cross-section of the lamp of FIG. 10 adapted to include a humidity control device and a temperature control device, according to non-limiting examples.

Similarly, at least the housing 1001, the removeable frame 1011, the various seals described above, the glass window 1507 and the transparent polymer film 1505 may be are ruggedized with respect to temperature over a range of one or more of about 0.1° C. to about 60° C. and about 0.1° C. to about 100° C. Furthermore, as depicted schematically, in FIG. 18, which is substantially similar to FIG. 13, with like components having like numbers, the lamp 123 may be adapted to include comprise one or more of a humidity control device 1850 and a temperature control device 1860 located inside the housing 1001, the humidity control device 1850 and the temperature control device 1860 being respectively similar to the humidity control device 750 and the temperature control device 760 described above. The humidity control device 1850 and the temperature control device 1860 may be particularly useful when the lamps 123 is one or more of airtight and watertight.

While a particular configuration for the lamp 123 has been described present examples include any type of lamp for illuminating food products along a line, comprising: a housing having a longitudinal axis and an opening along the longitudinal axis; a light source located in the housing along the longitudinal axis; a reflector positioned in the housing along the longitudinal axis, the reflector to reflect light from the light source through the opening and focus the light along the line; a removeable frame attached to the housing around the opening, the removeable frame having an aperture aligned with the opening along the longitudinal axis; a glass window in the aperture; a transparent polymer film in the aperture at an outward facing side of the glass window, each of the glass window and the transparent polymer film extending into the removeable frame past a perimeter of the aperture; and a seal between the transparent polymer film and the perimeter of the aperture.

Provided herein is a device and system for optically analyzing food products. The device includes a line-scan camera, a line-scan spectrometer, an optical filter and optional fold mirror which are used to simultaneously image food products at a line, as they are conveyed across the line. Spectroscopic images from the line-scan spectrometer may be used to determined quality of regions of the food products, and the images from the line-scan camera are coordinated with the spectroscopic images to locate regions of the food products having contaminants and/or given food product types. The system further includes a lamp for illuminating food products along the line, the lamp being sealed using a transparent polymer film in an aperture through which light is emitted, to enclose any shattering glass within the lamp.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, XZ, and the like). Similar logic can be applied for two or more items in any occurrence of "at least one . . . " and "one or more . . . " language.

The terms "about", "substantially", "essentially", "approximately", and the like, are defined as being "close to", for example as understood by persons of skill in the art. In some embodiments, the terms are understood to be "within 10%," in other embodiments, "within 5%", in yet further embodiments, "within 1%", and in yet further embodiments "within 0.5%".

Persons skilled in the art will appreciate that in some embodiments, the functionality of devices and/or methods and/or processes described herein can be implemented using pre-programmed hardware or firmware elements (e.g., application specific integrated circuits (ASICs), electrically erasable programmable read-only memories (EEPROMs), etc.), or other related components. In other embodiments, the functionality of the devices and/or methods and/or processes described herein can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative embodiments and modifications possible, and that the above examples are only illustrations of one or more embodiments. The scope, therefore, is only to be limited by the claims appended hereto.

What is claimed is:

1. A device for optically analyzing food products, the device comprising:
   a first imaging device sensitive to first wavelengths;
   a second imaging device sensitive to second wavelengths, one of the first imaging device and the second imaging device comprising:
   a line-scan camera configured to acquire images of food products in a human-visible wavelength spectrum, at a line in a food-path-facing direction,
   and an other of the first imaging device and the second imaging device comprising: a line-scan spectrometer configured to acquire spectroscopic images of the food products from the line in the food-path-facing direction;
   an optical filter configured to:
   convey the first wavelengths from the line to the first imaging device; and
   convey the second wavelengths from the line to the second imaging device; and
   a frame configured to align the optical filter and respective optical axes of the first imaging device and the second imaging device, relative to each other and the food-path-facing direction, such that the first imaging device and the second imaging device are optically aligned via the optical filter to image the line.

2. The device of claim 1, further comprising a conveyor located in the food-path-facing direction relative to both the respective optical axis of the first imaging device and the optical filter, the line located at the conveyor about perpendicular thereto.

3. The device of claim 1, wherein the respective optical axes of the first imaging device and the second imaging device are at about 90° to each other, and the optical filter is at about 45° to each of the respective optical axes, the optical filter further configured to:
   transmit the first wavelengths from the line to the first imaging device; and
   reflect the second wavelengths from the line to the second imaging device.

4. The device of claim 1, further comprising a fold mirror, wherein the frame is further configured to: align the respective optical axes of the first imaging device and the second imaging device at about 90° to each other; align the optical filter at about 45° to each of the respective optical axes; and align the fold mirror about parallel to the optical filter,
   wherein the fold mirror is positioned to:
   reflect the first wavelengths and the second wavelengths from the line to the optical filter, and
   wherein the optical filter is further configured to:
   reflect the first wavelengths from the fold mirror to the first imaging device; and
   transmit the second wavelengths from the fold mirror to the second imaging device.

5. The device of claim 4, further comprising a conveyor located in the food-path-facing direction relative to both the respective optical axis of the first imaging device and the optical filter, the line located at the conveyor about perpendicular thereto,
   wherein the fold mirror is positioned to reflect the first wavelengths and the second wavelengths at the conveyor to the optical filter from the food-path-facing direction towards the optical filter.

6. The device of claim 1, further comprising a removeable fold mirror, and the food-path-facing direction includes one of: a first food-path-facing direction; or a second food-path-facing direction about 90° to the first food-path-facing direction,
   wherein, when the removeable fold mirror is present, the removeable fold mirror reflects the first wavelengths and the second wavelengths of the line in the first food-path-facing direction to the optical filter; and the optical filter reflects the first wavelengths of the line in the first food-path-facing direction from the removeable fold mirror to the first imaging device and transmits the second wavelengths of the line in the first food-path-facing direction from the removeable fold mirror to the second imaging device; and
   wherein, when the removeable fold mirror is removed, the optical filter reflects the first wavelengths of the line in the second food-path-facing direction to the first imaging device and transmits the second wavelengths of the line in the second food-path-facing direction to the second imaging device.

7. The device of claim 6, further comprising one of:
   conveyor located in the first food-path-facing direction aligned with the respective optical axis of the first imaging device, the line located at the conveyor about perpendicular thereto; and
   a waterfall food product path in the second food-path-facing direction aligned with the respective optical axis of the second imaging device, the line located at the waterfall food product path about perpendicular thereto.

8. The device of claim 6, further comprising an enclosure configured to enclose the first imaging device, the second imaging device, the optical filter, the removeable fold mirror, and the frame, the enclosure including: a first aperture located in the first food-path-facing direction; and a second aperture located in the second food-path-facing direction, one of the first aperture and the second aperture covered by a window transparent to the first wavelengths and the second wavelengths, and the other of the first aperture and the second aperture covered by a cover.

9. The device of claim 8, wherein each of the window and the cover are removeable and attachable to either of the first aperture and the second aperture.

10. The device of claim 8, wherein the enclosure is ruggedized with respect to temperature over a range of one or more of about 0.1° C. to about 60° C. and about 0.1° C. to about 100° C.

11. The device of claim 8, wherein the enclosure is one or more of waterproof and resistant to disinfecting chemicals.

12. The device of claim 8, further comprising one or more of a humidity control device and a temperature control device located inside the enclosure.

13. The device of claim 1, further comprising an enclosure configured to enclose the first imaging device, the second imaging device, the optical filter, and the frame, the enclosure including a window transparent to the first wavelengths and the second wavelengths, the window positioned in the enclosure to convey the first wavelengths and the second wavelengths of the line to the optical filter.

14. The device of claim 13, wherein the enclosure ruggedized with respect to temperature over a range of one or more of about 0.1° C. to about 60° C. and about 0.1° C. to about 100° C.

15. The device of claim 13, wherein the enclosure is one or more of waterproof and resistant to disinfecting chemicals.

16. The device of claim 13, further comprising one or more of a humidity control device and a temperature control device located inside the enclosure.

* * * * *